US010123751B2

(12) United States Patent
Petterson et al.

(10) Patent No.: US 10,123,751 B2
(45) Date of Patent: Nov. 13, 2018

(54) SYSTEMS AND DEVICES FOR MOTION TRACKING, ASSESSMENT, AND MONITORING AND METHODS OF USE THEREOF

(71) Applicant: Strong Arm Technologies, Inc., Brooklyn, NY (US)

(72) Inventors: Sean Michael Petterson, Patchogue, NY (US); Michael Dohyun Kim, Sunnyside, NY (US); Alan Vito Argondizza, New York, NY (US); Michael Patrick Spinelli, Croton, NY (US)

(73) Assignee: StrongArm Technologies, Inc., Brooklyn, NY (US)

( * ) Notice: Subject to any disclaimer, the term of this patent is extended or adjusted under 35 U.S.C. 154(b) by 0 days.

(21) Appl. No.: 15/487,410

(22) Filed: Apr. 13, 2017

(65) Prior Publication Data

US 2017/0296129 A1    Oct. 19, 2017

Related U.S. Application Data

(60) Provisional application No. 62/321,865, filed on Apr. 13, 2016.

(51) Int. Cl.
*A61B 5/00* (2006.01)
*A61B 5/11* (2006.01)

(52) U.S. Cl.
CPC .......... *A61B 5/7275* (2013.01); *A61B 5/0022* (2013.01); *A61B 5/1118* (2013.01);
(Continued)

(58) Field of Classification Search
CPC ... A61B 5/7275; A61B 5/7405; A61B 5/1118; A61B 5/7278; A61B 5/7455;
(Continued)

(56) References Cited

U.S. PATENT DOCUMENTS 5,143,088 A * 9/1992 Marras ................... A61B 5/103
33/512
2007/0032748 A1    2/2007 McNeil et al.
(Continued)

FOREIGN PATENT DOCUMENTS

WO    2015153690 A1    10/2015
WO    2015164706 A1    10/2015

OTHER PUBLICATIONS

Marras et al., "Biomechanical risk factors for occupationally related low back disorders," ergonomics 1995, vol. 38, No. 2, 377-410.*
(Continued)

*Primary Examiner* — Rene Towa
(74) *Attorney, Agent, or Firm* — Greenberg Traurig, LLP

(57) ABSTRACT

A system includes a wearable sensor configured to be worn by a person and to record sensor data during an activity performed by the person; an analysis element configured to receive the sensor data from the wearable sensor, determine sensor orientation data of the wearable sensor during the activity based on the sensor data, translate the sensor orientation data of the wearable sensor to person orientation data of the person during the activity, determine, for the person during the activity, (a) a lift rate, (b) a maximum sagittal flexion, (c) an average twist velocity, (d) a maximum moment, and (e) a maximum lateral velocity, and determine a score representative of an injury risk to the person during the activity based on such data; and a tangible feedback element configured to provide at least one tangible feedback based on the score so as to reduce the injury risk.

23 Claims, 41 Drawing Sheets

(52) U.S. Cl.
CPC ............ *A61B 5/1121* (2013.01); *A61B 5/486* (2013.01); *A61B 5/6831* (2013.01); *A61B 5/7278* (2013.01); *A61B 5/742* (2013.01); *A61B 5/7405* (2013.01); *A61B 5/7455* (2013.01); *A61B 2562/0219* (2013.01)

(58) Field of Classification Search
CPC ....... A61B 5/6831; A61B 5/742; A61B 5/486; A61B 5/1121; A61B 5/0022; A61B 2562/0219
See application file for complete search history.

(56) References Cited

U.S. PATENT DOCUMENTS

| | | | |
|---|---|---|---|
| 2007/0186429 A1* | 8/2007 | Bonnet | A61B 5/1116 33/512 |
| 2007/0250286 A1* | 10/2007 | Duncan | A61B 5/1121 702/139 |
| 2009/0135009 A1* | 5/2009 | Little | G06Q 40/08 340/540 |
| 2009/0254003 A1* | 10/2009 | Buckman | A61B 5/1117 600/595 |
| 2010/0302142 A1 | 12/2010 | French et al. | |
| 2011/0201969 A1 | 8/2011 | Hatlestad et al. | |
| 2011/0208444 A1 | 8/2011 | Solinsky | |
| 2011/0230792 A1 | 9/2011 | Sarig-Bahat | |
| 2012/0038549 A1 | 2/2012 | Mandella et al. | |
| 2012/0094814 A1 | 4/2012 | Atkins et al. | |
| 2012/0158437 A1 | 6/2012 | Little et al. | |
| 2012/0232430 A1 | 9/2012 | Boissy et al. | |
| 2013/0103416 A1 | 4/2013 | Amigo et al. | |
| 2015/0065919 A1* | 3/2015 | Cuevas | A61B 5/1116 600/587 |
| 2016/0374608 A1* | 12/2016 | Dugan | A61B 5/6831 600/301 |

OTHER PUBLICATIONS

International Search Report and Written Opinion for PCT Application No. PCT/US2017/027508, dated Jun. 27, 2017.

Marras, W.S., et al, The role of dynamic three-dimensional trunk motion in occupationally-related low back disorders, SPINE, vol. 18, No. 5, pp. 617-628, 1993.

Marras, W.S., et al, Prospective validation of a low-back disorder risk model and assessment of ergonomic interventions associated with manual materials handling tasks, Ergonomics, vol. 43, No. 11, pp. 1866-1886, 2000.

Bernard, B.P. Musculoskeletal disorders and workplace factors, U.S. Department of Health and Human Services, chapter 6, pp. 6-1 to 6-96, 1997.

* cited by examiner

Warehouse 1 / Warehouse 2

PROBLEM
Choose one...
- ⊘ Lower Back Injuries
- ⊘ Hearing Problems
- ⊘ Slips, Trips, and Falls
- ⊘ Air Quality
- ⊘ Ambient Noise
- ⊘ Over Flexion ⊕ Create New Problem

INTERVENTION
Choose one...
- ⊘ FLx Ergoskeleton
- ⊘ FUSE Haptic Feedback
- ⊘ Personal Training See All Intervention Offers...
⊕ Create New Intervention

INTERVENTION DETAILS

DATA FACTORS
Choose one or more...
- ⊘ StrongArm Safety Score
- ⊘ Average Maximum Flexion
- ⊘ Average Twist Velocity
- ⊘ Lift Rate
- ⊘ Maximum Lateral Velocity
- ⊘ Maximum Moment

CONTINUE >

---

- FUSE
- Overview
- Athletes
- Shifts
- Job Functions

Logout

STRONGARM TECH

| Resolution | Metric | Reason Needed |
|---|---|---|
| Facility | LBD (injuries per person-hour incidence rate over time | Can be used to validate whether specific jobs are representative of entire facilities for LBD. |
| Individual | Injury history for individual | Whether an individual has had a prior injury greatly affects their movement and future likelihood of injury. Recommendations will also be affected. |
| Job | Injury data. OSHA 300 logs, LBD incidence rate over time | Crucial metric for evaluating ultimate risk of a specific job |
| Job | Changes, if any, to job over time | If the job has implemented an intervention prior to beginning use of analysis as described in the present disclosure, the historical injury data prior to that point will not be relevant. |
| Job | Turnover data for job (e.g., avg. tenure on job) | Turnover will affect the importance of injury statistics. If jobs have 0 injuries but have a new employee every month, that will be considered. |
| Individual | Productivity / throughput | Relevant for correlation with injury |
| Job | Average package weight. Max package weight. | Current knowledge indicates this is specifically important for predicting LBD risk |
| Job | Prior ergonomics assessment results (e.g., NIOSH lifting equation, RULA/REBA) | Alternative baseline risk model |
| Job | Volume / throughput | Relevant for determining whether higher-activity jobs are necessarily higher-injury jobs |
| Individual | Biometrics - Height, weight, age, sex, marital status, number of children, etc. | Parameters to use for predicting risk |
| Facility | Location | Possible injury factor |
| Facility | Indoor / outdoor temperature of facility | Possible injury factor |
| Facility | Employee satisfaction | Possible injury factor |
| Facility | Ergonomic budget | Possible injury factor |

| | | |
|---|---|---|
| Facility | Size (i.e., number of employees on-site) | Possible injury factor |
| Facility | Size (i.e., physical size of site) | Possible injury factor |
| Facility | Organizational chart structure/core team structure | Possible injury factor |
| Individual | Perception of danger or safety of job | Possible injury factor |
| Individual | Back pain rating of individual | Does the individual experience back pain frequently or at all? |
| Individual | Tenure at company and/or in current job | Injury risk can be affected by length of time at job |
| Individual | Job satisfaction | Predictive of high-risk jobs |
| Individual | Sleeping habits / average sleep | Possible injury factor |
| Individual | Frequency of changing job functions | Possible injury factor |
| Individual | Duration and type of commute | Possible injury factor |
| Individual | Physical activity level outside of work | Possible injury factor |
| Individual | Number of other jobs worked | Possible injury factor |
| Job | Employee satisfaction | Possible injury factor |

Fig. 14 Continued

SYSTEMS AND DEVICES FOR MOTION TRACKING, ASSESSMENT, AND MONITORING AND METHODS OF USE THEREOF

CROSS-REFERENCE TO RELATED APPLICATION

This application is a Section 111(a) application relating to and claiming the benefit of commonly owned, U.S. Provisional Patent Application No. 62/321,865, titled "MOTION TRACKING, ASSESSMENT, AND MONITORING," having a filing date of Apr. 13, 2016, the contents of which are incorporated by reference herein in their entirety.

FIELD OF THE INVENTION

The field of invention relates to monitoring of industrial athletes to ensure that they are working safely.

BACKGROUND OF THE INVENTION

Workplace injuries in the United States alone cost approximately $250 billion per year, a figure which is expected to rise over time. One prominent example is back injuries. Each back injury is estimated to cost almost $60,000 on average, totaling an estimated $120 billion a year. More importantly, beyond the mere financial cost of such injuries, is the debilitating pain suffered by those experiencing a workplace injury. Accordingly, there exists a need for improved systems and methods to prevent workplace injuries and, in particular, back injuries.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 12B is an exemplary display providing access to configure interventions that may be triggered based on a variety of problems;

FIG. 12C is an exemplary display providing access to various interventions that may be triggered for a selected problem;

FIG. 12D is an exemplary display providing access to various data factors that may be evaluated in triggering a selected intervention for a selected problem;

FIG. 12E is an exemplary display providing a selected problem, a selected intervention that may be triggered for the problem, and selected data factors that may be evaluated in triggering the selected intervention for the selected problem;

FIG. 12F is an exemplary display providing for input of information describing an intervention;

FIG. 12G is an exemplary display providing access to criteria that may be evaluated in determining whether to trigger an intervention;

FIG. 14 is an exemplary chart showing types of data that may be included in a database of historical information for use in predicting future injuries;

SUMMARY OF THE INVENTION

Figure 1:
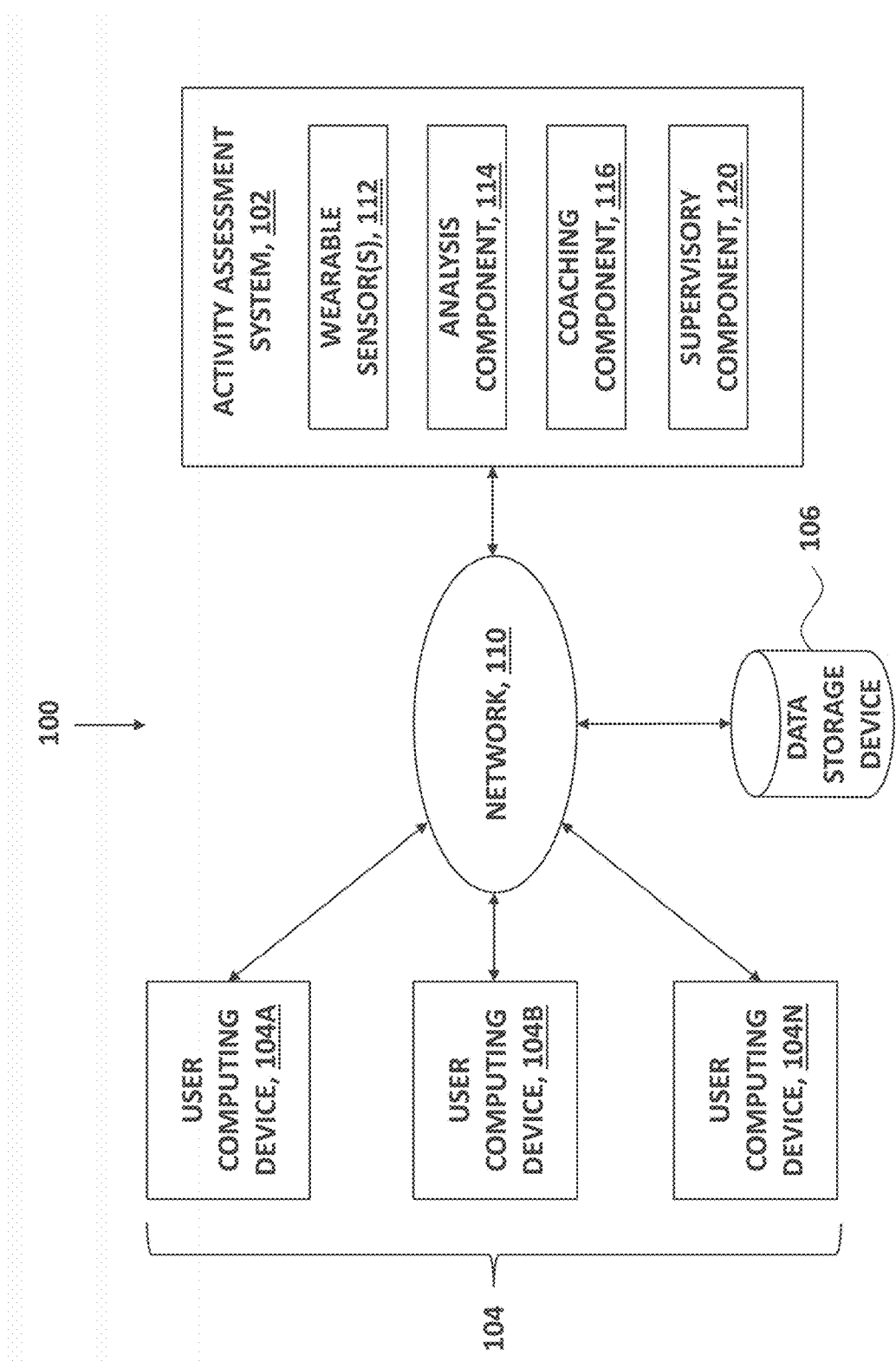
FIG. 1 is a schematic illustration of an operating environment for an activity assessment system that measures and analyzes movements of a user.

In some embodiments, a system includes a wearable sensor configured to be worn by a person and to record sensor data during an activity performed by the person, the sensor data comprising accelerometer data, gyroscope data, and magnetometer data; an analysis element configured to: receive the sensor data from the wearable sensor, determine sensor orientation data of the wearable sensor during the activity based on the sensor data, the sensor orientation data including (a) yaw data of the wearable sensor, (b) pitch data of the wearable sensor, and (c) roll data of the wearable sensor, translate the sensor orientation data of the wearable sensor to person orientation data of the person during the activity, the person orientation data including (a) yaw data of the person, (b) pitch data of the person, and (c) roll data of the person, the translating including using at least one Tait-Bryan rotation, determine, for the person during the activity, (a) a lift rate, (b) a maximum sagittal flexion, (c) an average twist velocity, (d) a maximum moment, and (e) a maximum lateral velocity based on at least (a) the yaw data of the person, (b) the pitch data of the person, and (c) the roll data of the person, and determine a score representative of an injury risk to the person during the activity based on (a) the lift rate, (b) the maximum sagittal flexion, (c) the average twist velocity, (d) the maximum moment, and (e) the maximum lateral velocity; and a tangible feedback element configured to provide at least one tangible feedback based on the score so as to reduce the injury risk, the at least one tangible feedback comprising at least one of (a) at least one haptic feedback, (b) at least one audible feedback, (c) at least one visible feedback, (d) at least one physical item to assist the person to perform the activity, and (e) at least one instruction to assist the person to perform the activity.

In some embodiments, the score is either a risk score that is configured to increase as the injury risk increases or a safety score that is configured to decrease as the injury risk increases. In some embodiments, tangible feedback element is integrated with the wearable sensor. In some embodiments, the tangible feedback element includes at least one of (a) at least one vibration motor configured to provide the at least one haptic feedback, (b) at least one speaker configured to provide the at least one audible feedback, (c) at least one display configured to provide the at least one visible feedback, and (d) at least one indicator light configured to provide the at least one visible feedback. In some embodiments, the tangible feedback element is configured to provide tangible feedback when the injury risk to the person exceeds a predetermined threshold.

In some embodiments, the determining, for the person during the activity, (a) the lift rate, (b) the maximum sagittal flexion, (c) the average twist velocity, (d) the maximum moment, and (e) the maximum lateral velocity is further based on body geometry. In some embodiments, the body geometry is body geometry of the person. In some embodiments, the body geometry is predetermined. In some embodiments, the wearable sensor includes an inertial measurement unit. In some embodiments, the wearable sensor includes a mobile phone.

In some embodiments, the physical item includes at least one of an ergosksleton, eye protection, ear protection, respiratory protection, foot protection, and hazardous materials protection, temperature protection, and fall protection. In some embodiments, the at least one instruction to assist the person to perform the activity includes training to perform the activity. In some embodiments, the at least one instruction to assist the person to perform the activity includes a scheduling change. In some embodiments, the scheduling change includes one of reassigning the person and switching the person with a further person.

In some embodiments, the system also includes a plurality of further wearable sensors configured to be worn by a plurality of further persons and to record sensor data during an activity performed by the further persons, the sensor data comprising accelerometer data, gyroscope data, and magnetometer data, wherein the analysis element is further configured to: receive the sensor data from each of the plurality of further wearable sensors, determine sensor orientation data of each of the plurality of further wearable sensors during the activity based on the sensor data received from each of the plurality of further wearable sensors, translate the sensor orientation data of each of the plurality of further wearable sensors to person orientation data of each of the plurality of further persons during the activity, the translating including using at least one Tait-Bryan rotation, determine, for each the further plurality of persons during the activity, (a) a lift rate, (b) a maximum sagittal flexion, (c) an average twist velocity, (d) a maximum moment, and (e) a maximum lateral velocity, and determine a further plurality of scores, each of which is representative of an injury risk to one of the further plurality of persons.

In some embodiments, the tangible feedback element is configured to provide tangible feedback to at least some of the further plurality of users based on the scores of the at least some of the further plurality of users. In some embodiments, the analysis element is further configured to determine an aggregate score for at least some of the further plurality of persons. In some embodiments, the at least some of the further plurality of persons are selected based on one of a job role, a full-time status, a duration of employment, a shift assignment, an injury history, a work location, a worker characteristic, a time of day, and a manual selection. In some embodiments, the tangible feedback element is configured to provide tangible feedback to the at least some of the further plurality of users based on the aggregate score.

In some embodiments, the activity includes performing at least one lifting action.

DETAILED DESCRIPTION OF THE INVENTION

Among those benefits and improvements that have been disclosed, other objects and advantages of this invention will become apparent from the following description taken in conjunction with the accompanying figures. Detailed embodiments of the present invention are disclosed herein;

however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In general, embodiments of the present disclosure are directed to systems and methods for tracking, assessment, and monitoring movements of workers. Tracking is accomplished by use of sensors that are mounted to the worker (e.g., chest, wrist, knee, etc.). In some embodiments, in which the wearable sensor 112 includes an inertial measurement unit ("IMU") sensor, the wearable sensor 112 records three-dimensional motions of the worker during the day, starting with measurements directly from the three integrated sensors of the IMU. In some embodiments, each sensor reading has an x, y, and z component, yielding a total of nine measurements per data point. In some embodiments, the IMU takes readings from an accelerometer, gyroscope, and magnetometer, each of which measurements has an x, y, and z component. In some embodiments, sensor fusion techniques are applied to filter and integrate the nine-component sensor measurements to calculate the orientation of the single wearable sensor 112 mounted to the worker. In some embodiments, the orientation that is calculated in this manner is described by three angles: yaw, pitch, and roll (herein collectively "YPR"). In some embodiments, a sensor fusion algorithm weights the data recorded by the accelerometer, gyroscope, and magnetometer of the IMU to calculate the orientation of the wearable sensor 112 in space using quaternion representation. In some embodiments, a sensor fusion algorithm includes a Kalman filter algorithm to process the recorded accelerometer, gyroscope, and magnetometer measurements, to minimize standard sensor noise, and to transform the quaternion representation into yaw, pitch, and roll data.

In some embodiments, the orientation of the wearable sensor 112 at any given moment in time can be described by considering an absolute reference frame of three orthogonal axes X, Y, and Z, defined by the Z-axis being parallel and opposite to the Earth's gravity's downward direction, the X-axis pointing towards the Earth's magnetic north, and the Y-axis pointing in a 90-degree counterclockwise rotation from the Z-axis. In some embodiments, the orientation of the wearable sensor 112 in space is described as a rotation from the zero-points of this absolute reference frame. In some embodiments, a Tait-Bryan chained rotation (i.e., a subset of Davenport chained rotations) is used to describe the rotation of the wearable sensor 112 from the zero points of the absolute reference frame to the orientation of the wearable sensor 112 in space. In some embodiments, the rotation is a geometric transformation which takes the yaw, pitch, and roll angles as inputs and outputs a vector that describes the orientation of the wearable sensor 112.

In some embodiments, the yaw, pitch, and roll angles that describe the spatial orientation of the wearable sensor 112 are used to calculate the yaw, pitch, and roll angles that describe the spatial orientation of the body of the individual to whom the wearable sensor 112 is mounted. In some embodiments, to perform this calculation, it is assumed that the wearable sensor 112 is rigidly fixed to the initially upright body of the wearer, and the Tait-Bryan chained rotation of the wearable sensor 112 is applied in reverse order, to the body, instead of to the wearable sensor 112. In some embodiments, the result of this rotation is a vector which can be considered to be the zero point of the body, to which the yaw, pitch, and roll angles of the wearable sensor 112 can be applied via a further Tait-Bryan chained rotation to calculate a vector that describes the orientation of the body in space at all times (i.e., a set of YPR values for the body). In some embodiments, parameters that are relevant to the ergonomics of the worker's motions, such as sagittal position, twist position, and lateral position. In some embodiments, a geometric calculation is performed on the set of YPR values for the body to determine the sagittal, twist, and lateral positions. In some embodiments, the sagittal, twist, and lateral positions are determined according to the following equations, with YPR values in degrees:

$$\text{Sagittal} = (-1 * \cos(\text{Roll})) * (90 - \text{Pitch})$$

$$\text{Lateral} = (-1 * \sin(\text{Roll})) * (90 - \text{Pitch})$$

In some embodiments, sagittal velocity and lateral velocity are then determined based on changes in the sagittal and lateral values over time. In some embodiments, change in twist is determined by projecting the pitch value into the XY plane (i.e., taking only the X and Y components of the pitch vector) and calculating the magnitude of change of the pitch value in that plane, thereby deriving twist velocity according to the following equation:

$$\text{Change in Twist} = \text{Sqrt}((\text{Change in Pitch } X)^2 + (\text{Change in Pitch } Y)^2)$$

In some embodiments, twisting velocity, lateral velocity, and sagittal flexion comprise three of the five values used in calculating a risk score, as will be described in further detail hereinafter.

In some embodiments, raw sensor data (e.g., as measured by the wearable sensor 112) is converted to body YPR data in accordance with the following process. In some embodiments, the process begins with a set of raw sensor readings from an accelerometer (a), gyroscope (g), and magnetometer (m) for a time range t=[0 . . . n]. Each of these sensor readings has an x, y, and z component:

$$\begin{bmatrix} a_{x0} & a_{y0} & a_{z0} & g_{x0} & g_{y0} & g_{z0} & m_{x0} & m_{y0} & m_{z0} \\ \vdots & \vdots & \vdots & \vdots & \vdots & \vdots & \vdots & \vdots & \vdots \\ a_{xn} & a_{yn} & a_{zn} & g_{xn} & g_{yn} & g_{zn} & m_{xn} & m_{yn} & m_{zn} \end{bmatrix}$$

In some embodiments, the above sensor readings are converted to the sensor's YPR at time t=[n] by Kalman filtering of the time window and sensor fusion algorithms which integrate the gyroscope and accelerometer values over time. In some embodiments, the gyroscope values are used to extrapolate the previous orientation at any given time to the predicted current orientation in the form of a quaternion. In some embodiments, the accelerometer and magnetometer values are then used as a baseline reference to the ground-frame to create a second quaternion. In some embodiments, these two quaternions are then combined in weighted fashion to create a more stable quaternion estimate of the orientation. In some embodiments, from this combined quaternion, YPR values for the sensor can then be inferred through known geometric techniques for converting quaternions to Euler angles. In some embodiments, such geometric techniques result in YPR values that describe the sensor at any time t=[n]:

$$(Yaw_{sensor,t=n}\ Pitch_{sensor,t=n}\ Roll_{sensor,t=n})$$

These values will hereinafter be abbreviated as:

$$(Y_{sn} P_{sn} R_{sn})$$

Figure 15:
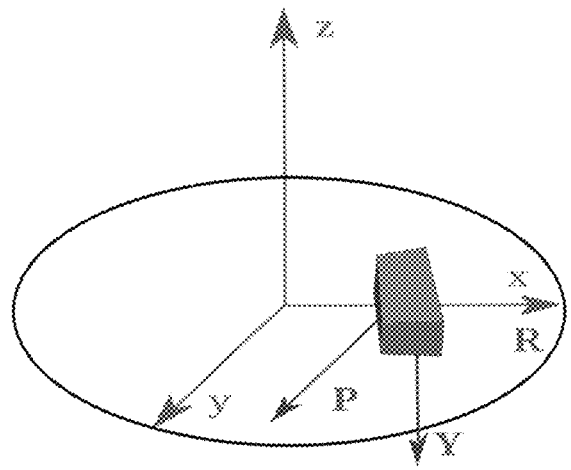
FIG. 15 is a first illustration of a sensor in space with reference to an absolute reference frame.

In some embodiments, the above values describe the orientation of the sensor in space, by considering their orientation as a rotation from a starting orientation aligned with an absolute reference frame. In some embodiments, the absolute reference frame consists of three orthogonal axes X, Y, and Z, defined by the Z-axis being parallel and opposite to the Earth's gravity's downward direction, and the X-axis pointing towards the Earth's magnetic north, as shown in FIG. 15.

In some embodiments, an absolute reference frame triad may be labeled (X, Y, Z) and the sensor's orientation may be labeled as (R, P, Y), which is a set of three vectors that describes the orientation of the sensor in space. If a reference frame triad can be denoted by:

$$X = \begin{bmatrix} 1 \\ 0 \\ 0 \end{bmatrix} Y = \begin{bmatrix} 0 \\ 1 \\ 0 \end{bmatrix} Z = \begin{bmatrix} 0 \\ 0 \\ 1 \end{bmatrix}$$

Then, by the above definition, the starting sensor orientation triad is:

$$R = \begin{bmatrix} 1 \\ 0 \\ 0 \end{bmatrix} P = \begin{bmatrix} 0 \\ 1 \\ 0 \end{bmatrix} Y = \begin{bmatrix} 0 \\ 0 \\ -1 \end{bmatrix}$$

In some embodiments, rotations by yaw, pitch, and roll angles can be considered to be a transformation of these triad vectors, as long as the transformation preserves orthogonality and length of the vectors. The yaw, pitch, and roll transformations can be represented by the angles Psi ($\psi$), Theta ($\theta$), and Phi ($\varphi$), respectively. It should be noted that ordering matters because it represents an order of operations; for example, if:

$$(Y_{sn}\ P_{sn}\ R_{sn}) = (-170°\ 45°\ 10°)$$

Figure 16:
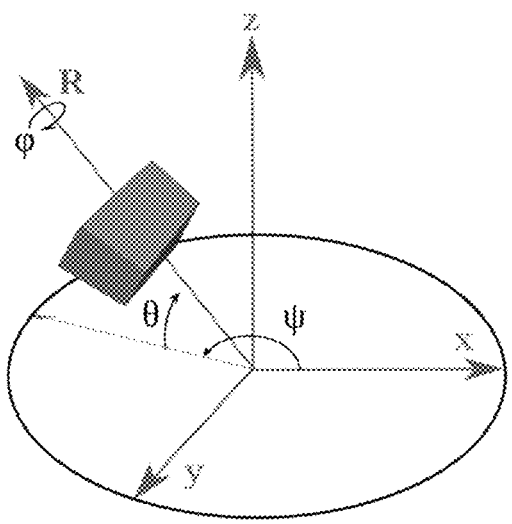
FIG. 16 is a second illustration of a sensor in space with reference to an absolute reference frame.

Then a sensor may be oriented as shown below, where first the rotation of the sensor about the yaw axis of the sensor orientation triad ($\psi=-170°$) is applied, then the rotation about the pitch axis of the sensor orientation triad ($\theta=45°$) is applied, and finally the rotation about the roll axis of the sensor orientation triad ($\varphi=10°$) is applied. It should be noted that yaw rotation ($\psi=-170°$) is negative in this case because the rotation is defined to be around the Y axis of the sensor orientation triad, and in this case the Y axis of the sensor orientation triad points in the opposite direction of the Z axis of the absolute reference frame triad. However, as shown in FIG. 16, the yaw rotation appears to be positive.

In some embodiments, rotations by angles Psi ($\psi$), Theta ($\theta$), and Phi ($\varphi$) as shown can be described as the product of three separate transformation matrices:

$$Yaw(\psi) = \begin{bmatrix} \cos(\psi) & -\sin(\psi) & 0 \\ \sin(\psi) & \cos(\psi) & 0 \\ 0 & 0 & 1 \end{bmatrix}$$

$$Pitch(\theta) = \begin{bmatrix} \cos(\theta) & 0 & -\sin(\theta) \\ 0 & 1 & 0 \\ \sin(\theta) & 0 & \cos(\theta) \end{bmatrix}$$

$$Roll(\theta) = \begin{bmatrix} 1 & 0 & 0 \\ 0 & \cos(\phi) & -\sin(\phi) \\ 0 & \sin(\phi) & \cos(\phi) \end{bmatrix}$$

The product of these transformation matrices may be referred to as M, as shown below:

$$M(\psi, \theta, \phi) = [Yaw(\psi)][Pitch(\theta)][Roll(\phi)]$$

$$M(\psi, \theta, \phi) =$$

$$\begin{bmatrix} \cos(\psi) & -\sin(\psi) & 0 \\ \sin(\psi) & \cos(\psi) & 0 \\ 0 & 0 & 1 \end{bmatrix} \begin{bmatrix} \cos(\theta) & 0 & -\sin(\theta) \\ 0 & 1 & 0 \\ \sin(\theta) & 0 & \cos(\theta) \end{bmatrix} \begin{bmatrix} 1 & 0 & 0 \\ 0 & \cos(\phi) & -\sin(\phi) \\ 0 & \sin(\phi) & \cos(\phi) \end{bmatrix}$$

It should again be noted that the order of the Yaw, Pitch, and Roll transformation matrices is in the order of operations, defined by the Tait-Bryan convention. This transformation matrix can be used to transform a vector V, as shown below:

$$TV = \begin{bmatrix} TV_x \\ TV_y \\ TV_z \end{bmatrix} = [M(\psi, \theta, \phi)] \begin{bmatrix} V_x \\ V_y \\ V_z \end{bmatrix}$$

In the above, the vector V could be the roll vector of the sensor orientation triad:

$$TV = [M(-170°, 45°, 10°)] \begin{bmatrix} 1 \\ 0 \\ 0 \end{bmatrix}$$

Where M is:

$$M(-170°, 45°, 10°) =$$

$$\begin{bmatrix} \cos(-170°) & -\sin(-170°) & 0 \\ \sin(-170°) & \cos(-170°) & 0 \\ 0 & 0 & 1 \end{bmatrix} \begin{bmatrix} \cos(45°) & 0 & -\sin(45°) \\ 0 & 1 & 0 \\ \sin(45°) & 0 & \cos(45°) \end{bmatrix}$$

$$\begin{bmatrix} 1 & 0 & 0 \\ 0 & \cos(10°) & -\sin(10°) \\ 0 & \sin(10°) & \cos(10°) \end{bmatrix}$$

Therefore, TV, the roll vector of the transformed sensor orientation triad, is:

$$TV = R_{transformed} = \begin{bmatrix} -0.696 \\ -0.123 \\ 0.707 \end{bmatrix}$$

These vector coordinates correspond to the roll vector's heading at a time where the sensor fusion algorithm reports the following YPR values:

$$(Y_{sn} P_{sn} R_{sn}) = (-170° \; 45° \; 10°)$$

In some embodiments, YPR values for the sensor are then converted to YPR values for the body, as discussed hereinafter. In some embodiments, such conversions are required because the sensor does not align with the axes of the body; in some embodiments, the sensor is mounted to the worker's chest, the same may be required in any case where the axes of the sensor are misaligned with the natural axes of the body. Therefore, in some embodiments, the body's YPR values are calculated based on the sensor's YPR values based on the assumptions that the sensor is rigidly fixed to the body and that there is a known value of the sensor's YPR values when the body is standing upright (i.e., the "neutral posture" in which the vertical axis of the body is parallel with the Z axis of the absolute reference frame). In some embodiments, neutral posture may be determined as will be described hereinafter. The sensor YPR values at the individual's neutral posture may be abbreviated as shown below:

$$(Y_{sp0} P_{sp0} R_{sp0})$$

As discussed above, the sensor's YPR values at any given time may be abbreviated as:

$$(Y_{sn} P_{sn} R_{sn})$$

The following set of calculations will be used to calculate the body's YPR values at any time, represented herein as:

$$(Y_{Bn} P_{Bn} R_{Bn})$$

As defined above, the starting sensor observation triad is as shown below:

$$R_{Body} = \begin{bmatrix} 1 \\ 0 \\ 0 \end{bmatrix} P_{Body} = \begin{bmatrix} 0 \\ 1 \\ 0 \end{bmatrix} Y_{Body} = \begin{bmatrix} 0 \\ 0 \\ 1 \end{bmatrix}$$

In some embodiments, to accomplish the required transformations, a vertical body vector is transformed "backwards" (i.e., roll, pitch, yaw instead of yaw, pitch, roll) by the angles that describe the sensor's orientation. The resulting orientation is the intermediate starting orientation of the body. Given the sensor readings at the body's neutral posture:

$$(\psi_{sp0}, \theta_{sp0}, \phi_{sp0}) = (Y_{sp0}, P_{sp0}, R_{sp0})$$

The starting orientation of the body can be calculated as:

$$[M_{reverse}(\phi_{sp0}, \theta_{sp0}, \psi_{sp0})][-Z] =$$

$$[Roll(\phi_{sp0})][Pitch(\theta_{sp0})][Yaw(\psi_{sp0})] \begin{bmatrix} 0 \\ 0 \\ -1 \end{bmatrix}$$

In the above, the vertical vector is negative because it is assumed that the body points straight upward in the global reference frame, which is straight downward in the starting YPR reference frame of the body. For example, if:

$$(\psi_{sp0}, \theta_{sp0}, \phi_{sp0}) = (Y_{sp0}, P_{sp0}, R_{sp0}) = (2°, 86°, 3°)$$

Then:

$$[M_{reverse}(\phi_{sp0}, \theta_{sp0}, \psi_{sp0})][-Z] = [Roll(3°)][Pitch(86°)][Yaw(2°)] \begin{bmatrix} 0 \\ 0 \\ -1 \end{bmatrix}$$

Which is equal to:

$$\begin{bmatrix} 1 & 0 & 0 \\ 0 & \cos(3°) & -\sin(3°) \\ 0 & \sin(3°) & \cos(3°) \end{bmatrix} \begin{bmatrix} \cos(86°) & 0 & -\sin(86°) \\ 0 & 1 & 0 \\ \sin(86°) & 0 & \cos(86°) \end{bmatrix}$$

$$\begin{bmatrix} \cos(2°) & -\sin(2°) & 0 \\ \sin(2°) & \cos(2°) & 0 \\ 0 & 0 & 1 \end{bmatrix} \begin{bmatrix} 0 \\ 0 \\ -1 \end{bmatrix}$$

Which is equal to:

$$R_{Body, intermediate} = \begin{bmatrix} 0.998 \\ 0.004 \\ -0.070 \end{bmatrix}$$

The above is the roll vector of the body's orientation triad which can be transformed by the YPR values of the sensor to obtain the neutral posture. The same operations are applied to the yaw and pitch axes of the body's orientation triad, which provides the below:

$$[[R_{Body}][P_{Body}][Y_{Body}]]_{intermediate}$$

This may then be transformed by the YPR values of the sensor to determine the body orientation triad's coordinates at any point in time:

$$[M(\psi_s, \theta_s, \phi_s)][[R_{Body}][P_{Body}][Y_{Body}]]_{intermediate}$$

Which is equal to:

$$[[R_{Body}][P_{Body}][Y_{Body}]]_n$$

Continuing with the above example, this operation would be performed as shown below:

$$[M(\psi_n, \theta_n, \phi_n)][R_{Body, intermediate}]$$

Which is equal to:

$$\begin{bmatrix} \cos(-170°) & -\sin(-170°) & 0 \\ \sin(-170°) & \cos(-170°) & 0 \\ 0 & 0 & 1 \end{bmatrix} \begin{bmatrix} \cos(45°) & 0 & -\sin(45°) \\ 0 & 1 & 0 \\ \sin(45°) & 0 & \cos(45°) \end{bmatrix}$$

$$\begin{bmatrix} 1 & 0 & 0 \\ 0 & \cos(10°) & -\sin(10°) \\ 0 & \sin(10°) & \cos(10°) \end{bmatrix} \begin{bmatrix} 0.998 \\ 0.004 \\ -0.070 \end{bmatrix}$$

Which is equal to:

$$R_{Body, t=n} = \begin{bmatrix} -0.740 \\ -0.140 \\ 0.657 \end{bmatrix}$$

In some embodiments, YPR values that transform the body itself are determined, where the body's YPR triad vectors are as defined as starting in alignment to the global absolute reference frame. In the above, the roll vector of the body orientation triad protrudes from the individual's head, parallel with the line drawn from navel to head, the pitch vector of the body orientation triad protrudes from the individual's left side, perpendicular to both the roll vector and the yaw vector, and the yaw vector protrudes from the individual's back, perpendicular to the plane of the back, and perpendicular to the roll vector. In some embodiments, to obtain YPR transformation angle values, the below equation is solved for the values Psi ($\psi$), Theta ($\theta$), and Phi ($\varphi$):

$$R_{Body,t=n} = \begin{bmatrix} -0.740 \\ -0.140 \\ 0.657 \end{bmatrix} = [M(\psi, \theta, \phi)] \begin{bmatrix} 1 \\ 0 \\ 0 \end{bmatrix}$$

Figure 17:
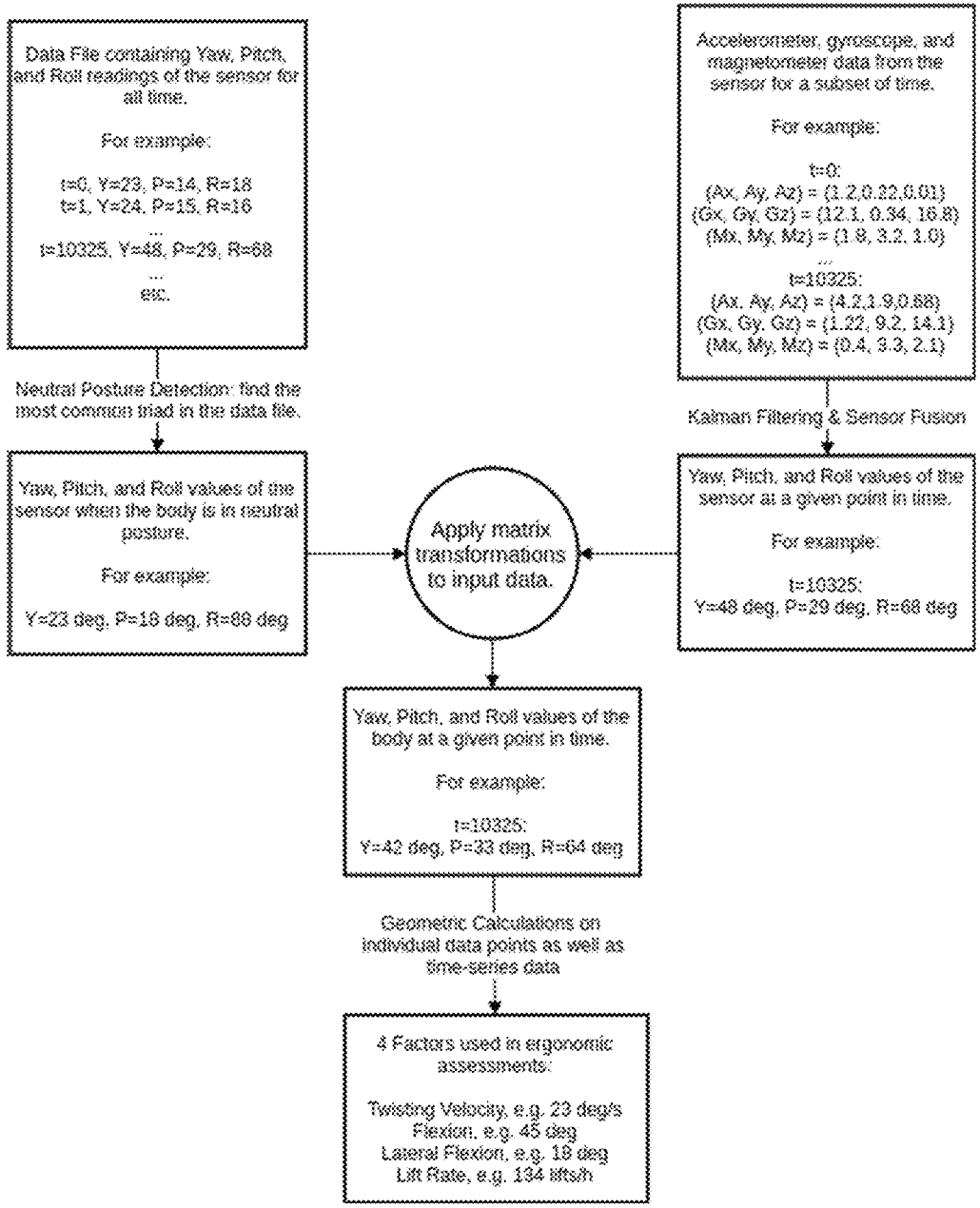
FIG. 17 is a flowchart of an exemplary data analysis method.

It should be noted that the equation above produces one equation with three unknowns, and it is impossible to solve this without two other equations. In some embodiments, the two other equations are obtained by following the same procedure for the $Y_{Body}$ and $P_{Body}$ vectors, first finding $Y_{Body, intermediate}$ and $P_{Body, intermediate}$ and then calculating $Y_{Body, t=n}$ and $P_{Body, t=n}$. Following this procedure results in three equations with three unknowns Psi ($\psi$), Theta ($\theta$), and Phi ($\varphi$) which can be solved to find yaw ($\psi$), pitch ($\theta$), and roll ($\varphi$) transformations that describe the orientation of the body in space at any given point in time t=[n]. FIG. 17 shows a flowchart embodying the performance of the above-described calculations for one exemplary data point.

In some embodiments, these motions are further assessed, on an individual and/or aggregate basis, according to selected kinematic models to characterize motion risks (e.g., along a sliding numeric scale, along a qualitative low-medium-high scale, etc.). Aggregate risk scores or safety scores may be further generated from these kinematic models. In some embodiments, kinematic models are defined based on knowledge of ergonomics and how these motions apply to influence a human body and its development (e.g., healing, compensation, human behavior, etc.) over time. In some embodiments, data collected based on wearers' motions can be applied to real-world management applications, including prediction of injuries, workforce optimization, recommended safety activities or equipment which have a known positive impact, and other organizational re-routing to optimize an organization for safe working conditions in connection with worker cost and productivity. In some embodiments, activities taken to manage a workforce in accordance with the above will have a known and quantifiable impact. In some embodiments, aggregate risk scores are determined for groups of individuals that are selected based on one or more of job role, full-time status, duration of employment, shift assignment, injury history, work location, worker characteristics, time of day, and/or manual selection.

The measured motions and/or risk scores may be further displayed for use. In one embodiment, the measured motions and/or risk scores may be displayed to the worker to heighten their awareness of the measured motion risk. Optionally, based upon the assessed risk, the worker may be further provided with coaching advice for reducing motion risk. In another embodiment, the measured motions and/or risk scores for individual workers, groups of workers in aggregate, and combinations thereof, may be displayed to a supervisor.

The discussion will now turn to FIG. 1, which illustrates an embodiment of an operating environment 100 for measurement, assessment, and monitoring of worker motions. The environment 100 includes an activity assessment system 102, a plurality of user computing devices 104 (104A, 104B, . . . 104N), and a data storage device 106, each in communication via a network 110. The activity assessment system 102 includes a plurality of wearable sensors 112, an analysis component 114, a coaching component 114, and a supervisory component 120. It may be understood that, while the activity assessment system 102 is described herein in the context of bending of the back (i.e., lumbar flexion), embodiments of the disclosure may be directed to any desired body kinematics.

Embodiments of the user computing devices 104 may be independently selected any computing device such as desktop computers, laptop computers, mobile phones, tablet computers, set top boxes, entertainment consoles, server computers, client computers, and the like. In further embodiments, the activity assessment system 102 and one or more of the user computing devices 104 may be integrated within a single device.

Embodiments of the data storage device 106 may include one or more data storage device capable of maintaining computer-readable data. Examples may include, but are not limited to, magnetic storage (e.g., tape, hard disk drives, etc.), solid-state storage (e.g., flash memory, etc.), and other computer-readable media.

Embodiments of the network 110 may include, but are not limited to, packet or circuit-based networks. Examples of packet based networks may include, but are not limited to, the Internet, a carrier internet protocol (IP) networks (e.g., local area network (LAN), wide area networks (WAN), campus area networks (CAN), metropolitan area networks (MAN), home area networks (HAN), a private IP networks, IP private branch exchanges (IPBX), wireless networks (e.g., radio access network (RAN), IEEE 802.11 networks, IEEE 802.15 networks, IEEE 802.16 networks, general packet radio service (GPRS) networks, HiperLAN, etc.), and/or other packet-based networks. Examples of circuit-based networks may include, but are not limited to, the public switched telephone networks (PSTN), a private branch exchanges (PBX), wireless network (e.g., RAN, Bluetooth™, code-division multiple access (CDMA) networks, time division multiple access (TDMA) networks, Enhanced Data rates for GSM Evolution (EDGE) networks, global system for mobile communications (GSM) networks), and/or other circuit-based networks.

Data transmission and instructions can also occur over the network 110. Information carriers suitable for embodying computer program instructions and data include all forms of non-volatile memory including, by way of example, semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

Figure 2:
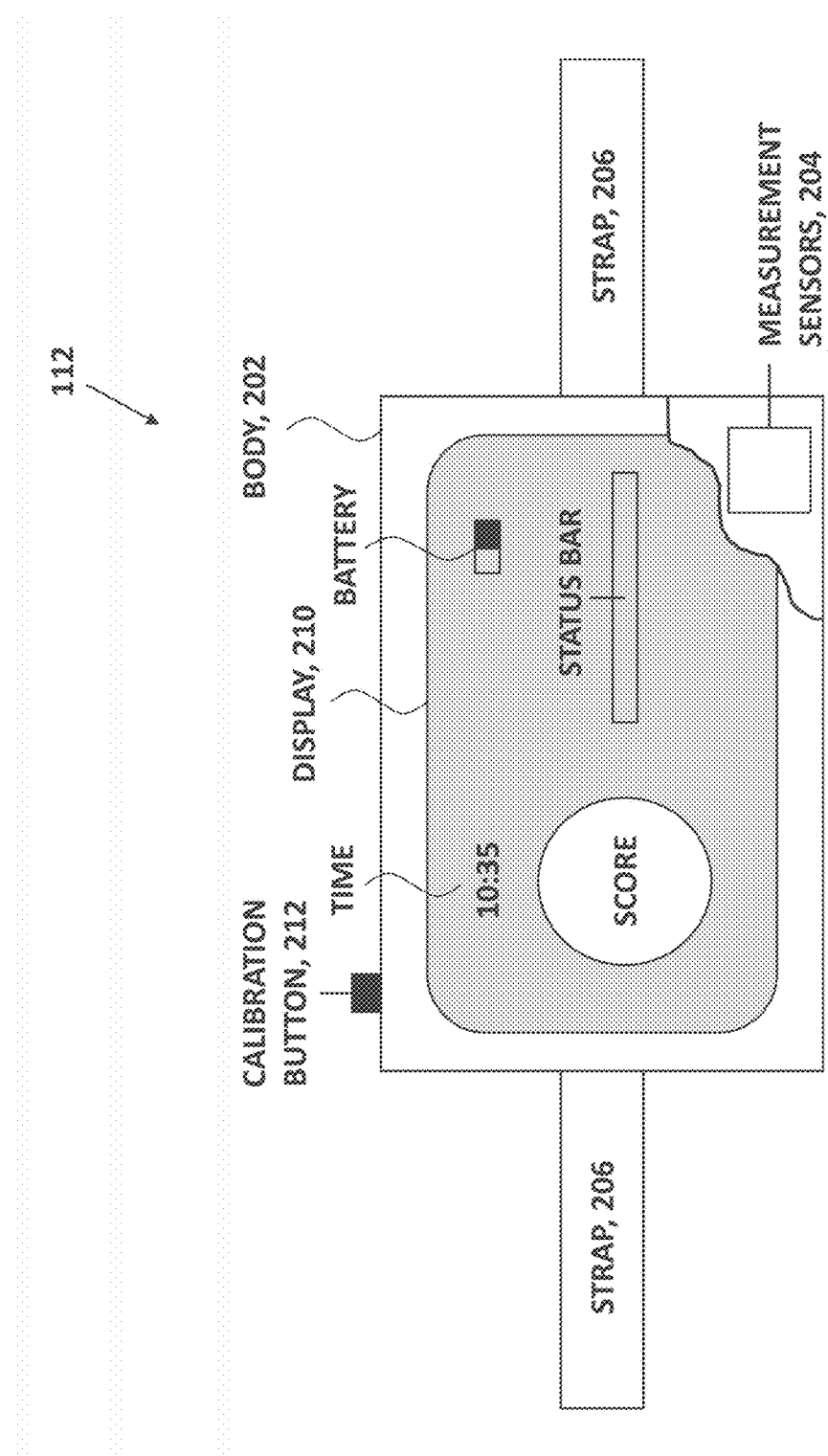
FIG. 2 is a schematic illustration of an embodiment of a measurement device including a plurality of sensors for measuring movements of the user.

An embodiment of the wearable sensor 112 is illustrated in FIG. 2. The wearable sensor 112 includes a body 202 housing a plurality of measurement sensors 204. Embodiments of the measurement sensors 204 include any devices capable of measuring body kinematics. Examples include, but are not limited to, one or more of gyroscopes, magnetometers, accelerometers, barometers, tilt switches, vibration switches, cameras, photoresistors, ultrasonic rangefinders, infrared rangefinders, structured light projections, electromyographs, and the like. In further embodiments, the wearable sensor 112 include one or more data storage devices (not illustrated) for transient or permanent local storage of kinematic data recorded by the measurement sensors 204. In some embodiments, the wearable sensor 112 is a mobile phone programmed to operate as described herein (e.g., by installation of a suitable "app").

In an embodiment, the body 202 may be mechanically engaged with a strap 206 (e.g., a hook and loop fastener) for securing the wearable sensor 112 to the worker. It may be understood that, in alternative embodiments, the strap 206 may be omitted or used in combination with other reversible fastening devices, such as adhesives, clips, pins, suction devices, etc.

In certain embodiments, the wearable sensor 112 includes one or more data processors (not illustrated) for analysis of kinematic data recorded by the measurement sensors 204. In other embodiments, the wearable sensor(s) may include a wireless transmitter (e.g., Wi-Fi™, Bluetooth™, etc.) or wired interface (e.g., USB™) for transmission of data to a computing device (e.g., the user computing device(s) 104) for analysis and/or storage measured kinematic data.

In further embodiments, the wearable sensor 112 includes a display 210 for showing analyzed data to the worker. For example, as discussed in greater detail below, the display 210 may show at least one of a movement score and a status bar, as well as ancillary information such as time and battery life. The movement score is obtained from analysis of the worker's movements on a pre-determined scale. The status bar may further characterize a quality of the worker's movements (e.g., low risk, moderate risk, high risk) based upon the analyzed score. In this manner, the worker is provided with real-time information regarding their movements. In additional embodiments, the wearable sensor 112 may additionally include a notification mechanism (not illustrated) that provides one or more of audio, visual, and tactile signals (e.g., speakers, lights, vibration motors, etc.) to warn the worker when the quality of their analyzed movements is characterized as moderate and/or high risk.

In additional embodiments, the wearable sensor 112 may additionally include a calibration button 212 for performing a calibration process, as discussed in greater detail below.

Figure 9:
FIG. 9 is a photograph of an embodiment of a wearable sensor.

In some embodiments, the wearable sensor 112 includes a 9-degree-of-freedom inertial measurement unit ("IMU") operative to record three-axis accelerometer data, three-axis gyroscope data, and three-axis magnetometer data. FIG. 9 is a photograph of an exemplary wearable sensor 112. In some embodiments, the IMU is integrated with a mobile phone. In some embodiments, the wearable sensor 112 includes another suitable type of sensing apparatus that is operable to determine yaw/pitch/roll measurements, as will be described hereinafter. In some embodiments, the wearable sensor 112 includes a battery having 19 hours of battery life or more. In some embodiments, the wearable sensor 112 is configured to communicate by Bluetooth. In some embodiments, the wearable sensor 112 is configured to communicate by WiFi. In some embodiments, the wearable sensor 112 includes a processor that is operable to support data processing, data transfer, and data visualization in real time. In some embodiments, the wearable sensor 112 can be "checked out" and "checked in," allowing a single one of the wearable sensor 112 to be shared among different users throughout the day. In some embodiments, the wearable sensor 112 includes at least one component capable of providing user feedback. In some embodiments, the wearable sensor 112 includes a vibration motor capable of providing tactile/haptic feedback. In some embodiments, the wearable sensor includes a speaker capable of providing auditory feedback. In some embodiment, the wearable sensor includes at least one LED capable of providing visual feedback. In some embodiments, the wearable sensor 112 is provided with a strap 206 that is one-size-fits-all and unisex. In some embodiments, the strap 206 has a one-point attachment mechanism. In some embodiments, the strap 206 has three adjustment points. In some embodiments, rather than using a wearable sensor 112, the system 100 may include external sensors (e.g., an optical sensing system with dot trackers, video analysis, etc.) that are operable to determine yaw/pitch/roll measurements, as will be described hereinafter.

Figure 10:
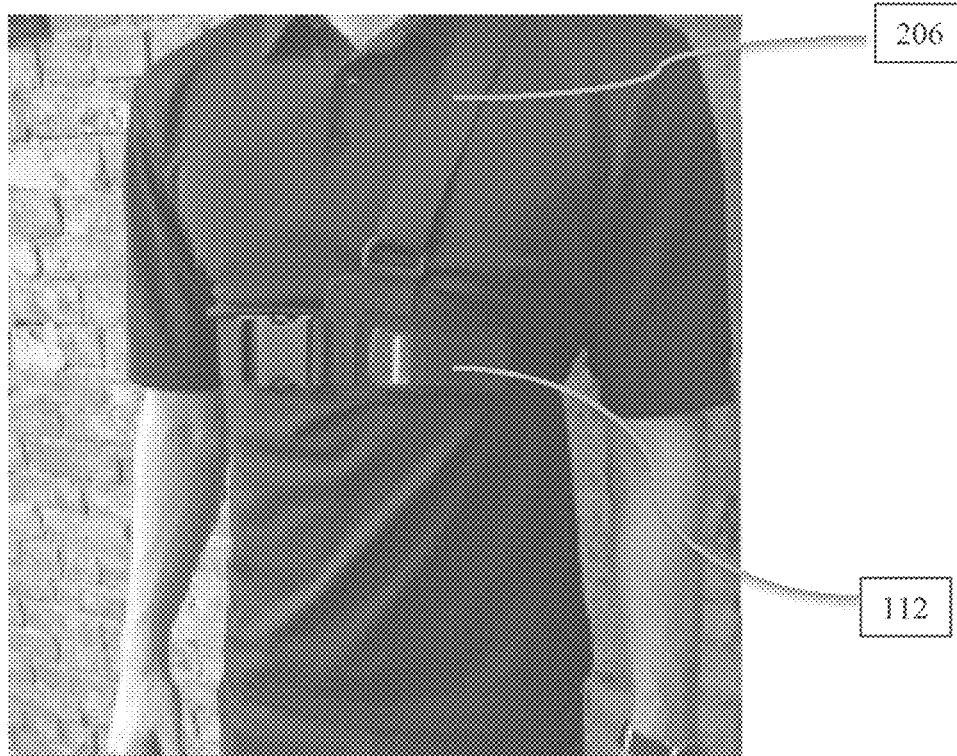
FIG. 10 is a photograph of the wearable sensor of FIG. 9, as incorporated into a strap and worn by an individual.

In some embodiments, the wearable sensor 112 is adapted to be worn in a location that maximizes user comfort, ease of adjustment, and the accuracy of the data output. In some embodiments, the wearable sensor 112 is adapted to be worn directly below the pectoral on the anterior side. In some embodiments, a wearable sensor 112 that is worn directly below the pectoral on the anterior side is comfortable to wear, is capable of capturing the information described herein, and is easy for the user to quickly don and remove. In some embodiments, the location of the wearable sensor 112 on the body is predetermined and calculations are based on the predetermined location of the wearable sensor 112. In some embodiments, the algorithm is adjustable based on the location of the wearable sensor 112. In some embodiments, the wearable sensor 112 is worn on the left side. In some embodiments, the wearable sensor 112 is worn on the right side. In some embodiments, the wearable sensor 112 may be worn on either the left side or the right side, provided that it is positioned on a known horizontal plane. In some embodiments, a wearable sensor 112 that is adapted to be worn directly below the pectoral on the anterior side provides the wearer with a visual connection to the device and provides for easy attachment, removal, and adjustment. In some embodiments, a wearable sensor 112 that is adapted to be worn directly below the pectoral on the anterior side provides for consistent position readings and does not interfere with arm mobility. In some embodiments, a wearable sensor 112 that is adapted to be worn directly below the pectoral on the anterior side minimizes unwanted movement between the sensor and the wearer's body and does not provide uncomfortable contact with the wearer's neck. FIG. 10 is a photograph of an exemplary wearable sensor 112, as engaged with a strap 206 and worn by a user in the position described above.

Figure 3:
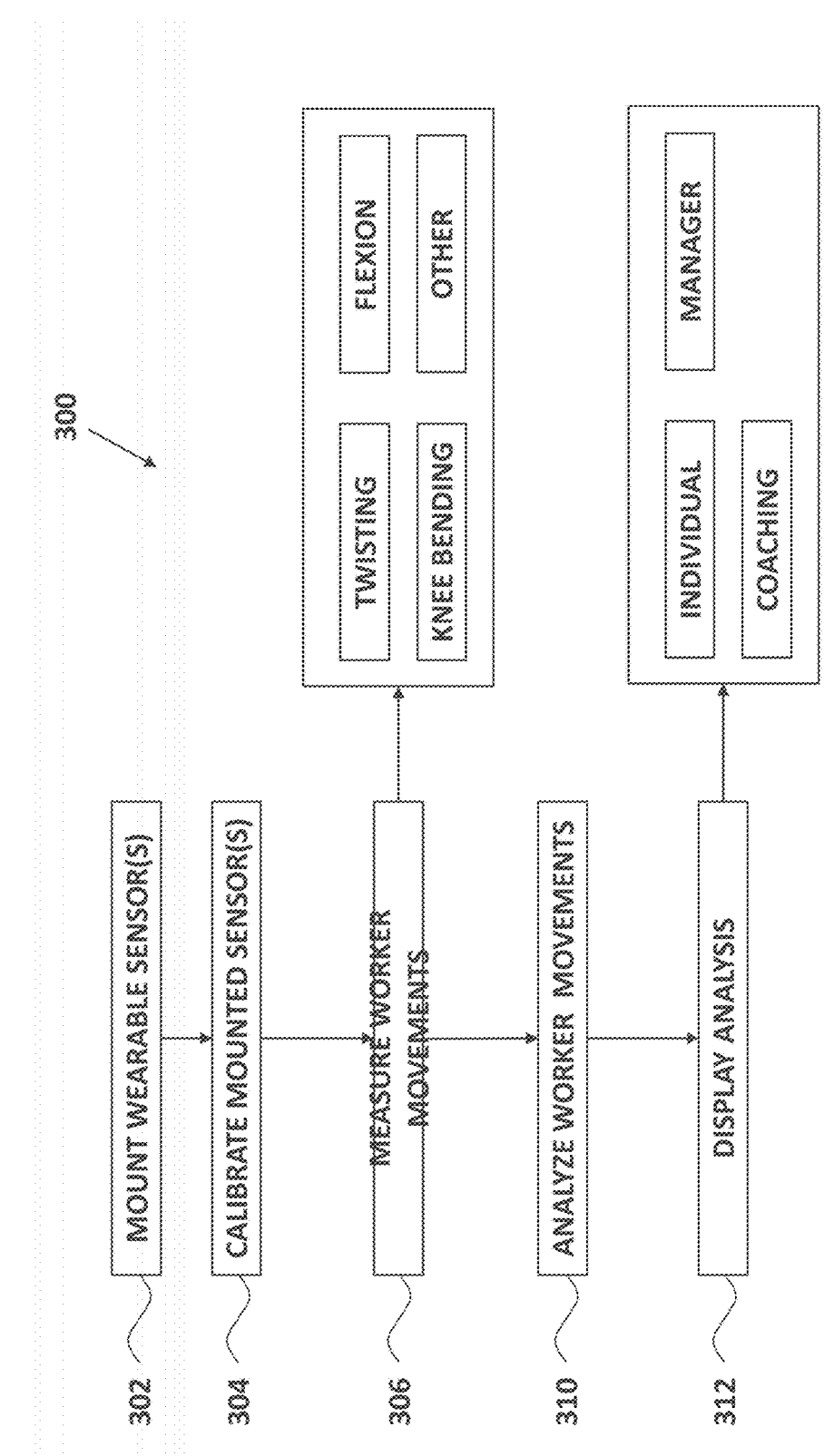
FIG. 3 is a flow diagram illustrating an embodiment of a method for measuring a worker's movements employing the measurement device of FIG. 2.

An embodiment of a method 300 for measuring, assessing, and monitoring a worker's movements is illustrated in FIG. 3. The method 300 includes mounting the wearable sensors 112 in operation 302, calibrating the mounted sensors in operation 304, measuring the worker's movements in operation 306, analyzing the worker's movements in operation 310, and displaying the analysis in operation 312.

In operation 302, the wearable sensor(s) 112 are mounted to the worker. As discussed above, the wearable sensor 112 is securely mounted at a desired location on the body, such as the worker's chest or wrist. In further embodiments, the wearable sensor 112 may be mounted to the worker's back, torso, hip, or ankle.

In operation 304, the wearable sensor 112 is calibrated. For example, the worker presses the calibration button 212, while standing upright and still (i.e., in a neutral posture), to begin the calibration process. During the calibration process, measurements of the worker's upright posture are determined by an average of many posture measurements. In certain embodiments, the notification mechanism (e.g., an audible tone, light, and/or vibration) indicates that the calibration process is ongoing. For example, in the case where the notification mechanism is a speaker, a series of beeps of one tone are emitted while the calibration process is ongoing, while a single beep of a second tone is emitted to indicate that the calibration process has ended successfully. If the worker moves or does not stand upright during the calibration process, the speaker may emit a single beep of a third tone to indicate an unsuccessful calibration.

In further embodiments, if the calibration process is initiated and there is a recorded measurement from the previous calibration, the average of posture measurements is compared to the previously recorded measurement after collecting small number of samples. Negligible difference between these two numbers results in the successful end of the calibration process. Beneficially, this process minimizes redundancy of sampling posture measurements when the same worker uses the same wearable sensor 112. Additionally, this process serves to encourage workers to stand upright for the calibration process by rewarding shorter calibration duration. Conversely, if the difference between these two numbers is significant, the calibration process takes sufficient posture measurements to determine the worker's upright posture, as discussed above.

In some embodiments, rather than including a dedicated calibration step in operation 304, calibration to determine a wearer's neutral posture may be accomplished using data recorded while the wearer is moving (as described below with reference to step 306). A neutral posture acts as a point of reference for subsequent determinations regarding the relative motion of the wearers body. In some embodiments, the lack of a separate calibration step may be preferable because workers may not wish to stay still wait for the wearable sensor 112 to be calibrated. In some embodiments, neutral posture detection is determined by reviewing yaw data, pitch data, and roll data recorded by the wearable sensor 112. In some embodiments, neutral posture detection includes determining the values for yaw, pitch, and roll that occurred most often in the data for each variable. In some embodiments, neutral posture detection includes identifying, as the neutral posture, the values for yaw, pitch, and roll that occur most often (i.e., the position in which the wearer spends the most time) in the data for each variable (i.e., the mode of the data). In some embodiments, values for yaw, pitch, and roll are smoothed and rounded prior to determining the most frequent value in order to provide consistency and eliminate noise inherent in sensor measurements.

For example, the below table presents an example set of data for an individual who stands in three different positions (for clarity, only pitch and roll are shown, but the same concepts will be equally applicable to an analysis including yaw, pitch, and roll):

| Position | Time Spent at Position | Pitch Angle at Position | Roll Angle at Position |
| --- | --- | --- | --- |
| A | 10 minutes | 10 degrees | 10 degrees |
| B | 10 minutes | 10 degrees | 12 degrees |
| C | 15 minutes | 23 degrees | 45 degrees |

In some embodiments, the neutral posture is assessed to be (Pitch=10 degrees, Roll=45 degrees) because these are the individual pitch and roll values that are the most common. In some embodiments, the neutral posture is assessed to be the combination of yaw, pitch, and roll that is most common. In such embodiments and considering the above data, the neutral posture is assessed to be (Pitch=23 degrees, Roll=45 degrees), because this is the combination of pitch and roll values that is the most common. In some embodiments, the latter assessment may provide a better assessment of the individual's most common posture, which may be deemed the neutral posture.

In some embodiments, smoothing and rounding of the yaw, pitch, and roll data are performed in accordance with a normalization process. In some embodiments, normalization occurs only once, upon ingest of the data, before processing for analysis. In some embodiments, as a result, a simpler system architecture is required in order to process, store and generally present the information in an easy-to-understand fashion. In some embodiments, normalization need not be performed before each separate analysis. In some embodiments, as a result, maintenance activities take less time because software implementing normalization is stored in a consistent location and codebase. In some embodiments, performing normalization at the time of data intake assists with scaling the solution across multiple pipelines of data, as each stream of data information can be trusted to be "clean" and free of defects, dramatically reducing the time to market for new features and capabilities. As a result, in some embodiments, customers are presented with greater value, a more robust service, reduced cost, and with faster delivery of new features.

In operation 306, the wearable sensor 112 measures movements of the worker over any range of motion. For example, in the case where the wearable sensor 112 is mounted to the user's chest, the position of the worker's back and the angle of the back with respect to the ground as a function of time. Such measurements may be taken at discrete time intervals or continuously. The measured worker movement data is saved to the data storage device 106 locally or remotely for subsequent analysis. For example, the measured worker movement data may be sent automatically to a remote data storage device 106 in response to a triggering signal (e.g., a request to synchronize the wearable sensor 112) or by connecting the wearable sensor 112 to a computing device or power source.

In further embodiments, movement of the worker's knees may be inferred from measurements taken by the wearable sensor 112 when mounted to the worker's chest. For example, the measurements taken by the wearable sensor 112 may be used to determine if the worker is performing one or more movements including, but not limited to, walking, running, jumping, squatting, standing upright, twisting their torso, pivoting around one foot, reaching above their head, and riding in a vehicle. The classification of worker movements into groupings of activities such as these may be performed by one or more of the following: machine learning techniques such as logistic regression or linear regression, machine learning tools such as neural networks or support vector machines that have been trained to recognize movement patterns based on a dataset of manually classified movements.

Figure 4A:
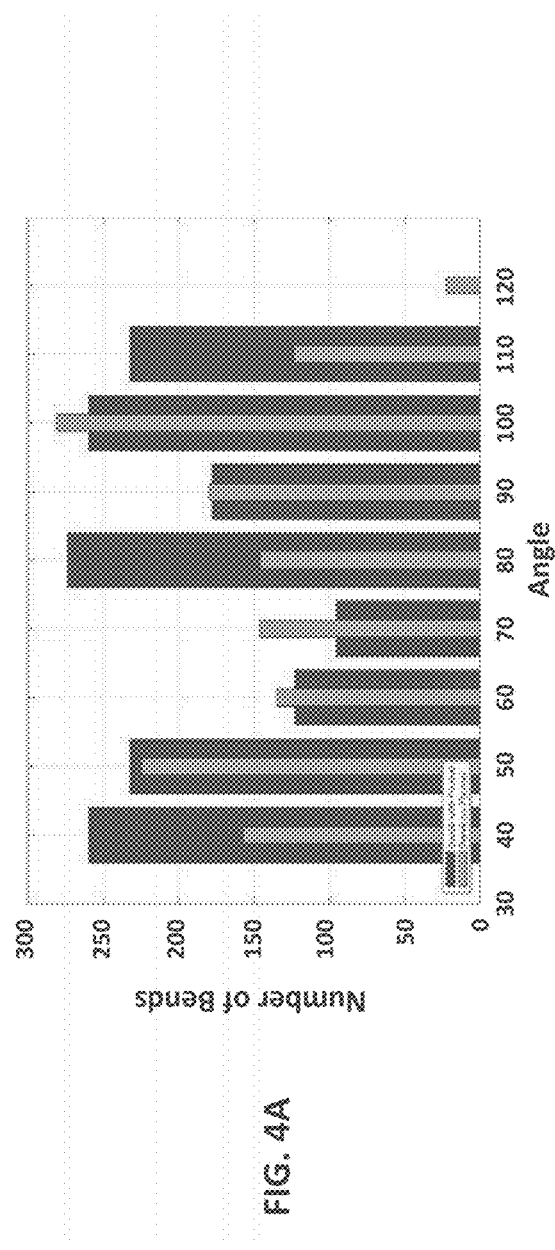
FIGS. 4A-4B are plots illustrating bending activity of a user as measured according to embodiments of the system of FIG. 1.
Figure 4B:
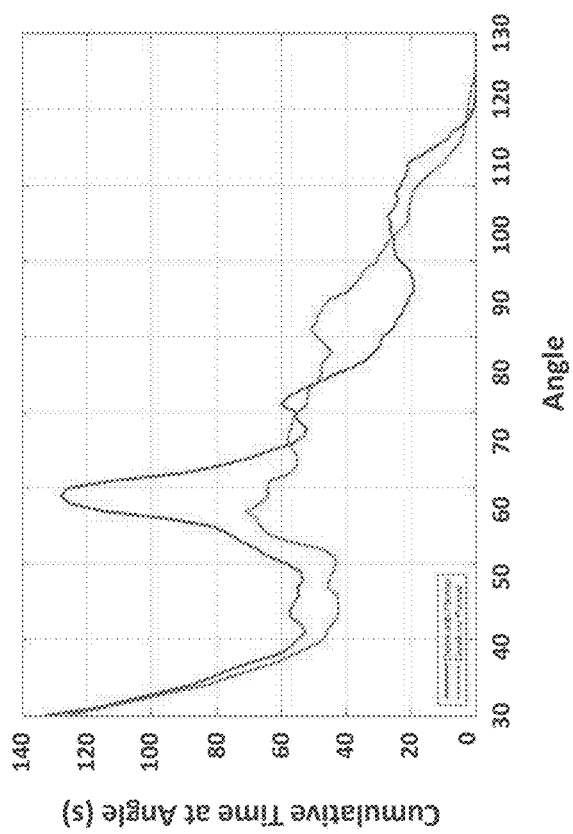

Examples of measured data are illustrated in FIGS. 4A-4B. FIG. 4A is a plot of number of bends (normalized to 8 hours) as a function of angle. A complementary representation, illustrated in FIG. 4B, plots cumulative time (in seconds, normalized to 8 hours) as a function of angle. It may be observed that motions within the range of 40 degrees-50 degrees are frequent and held for a brief time, while motions within the range of 60 degrees-70 degrees occur less frequently but are held for a longer time. Motions within the range of 80 degrees-130 degrees occur less frequently and are held for a brief time. From this, it may be inferred that bends occurring frequently and for long times represent the position a worker adopts when carrying an object, while bends occurring frequently or infrequently for short times represent transitions while an object is being lifted. In general, a worker exhibiting good lifting technique will spend higher amounts of time at lower angles, while a worker exhibiting bad lifting technique will show a higher amount of time at higher angles.

In operation 310, the worker's measured movements are analyzed. As discussed above, in certain embodiments, the analysis may be performed by a processor of the wearable sensor 112 itself. In alternative embodiments, the analysis may be performed by another computing device (e.g., one or more of user computing devices 104) or a remote server that. In the case of analyses performed by a remote server, the results may be further transmitted to one or more of user computing devices 104.

In some embodiments, operation 310 includes detection of the frequency of lifts by a worker who is wearing the wearable sensor 112. The frequency of lifting is a major component of determining one's risk of lower back injury. Lifting may typically involve forward bending. In some embodiments, a lift is identified by identifying a peak in a worker's forward sagittal flexion motion. In some embodiments, when a peak in a worker's forward sagittal flexion motion occurs, a lift is identified. In some embodiments, a lift is detected based on two values: minimum peak height ("MPH") and minimum peak prominence ("MPP"), both of which are applied to the sagittal flexion angle. In some embodiments, a MPH is 30 degrees sagittal flexion and a MPP is 40 degrees sagittal flexion. In some embodiments, MPH is the minimum sagittal angle that must be achieved before a lift can be detected; for example, if MPH is 30 degrees, if the sagittal flexion never exceeds 30 degrees, no lifts are detected. In some embodiments, MPP is the minimum difference between a local maximum and the nearest local minimum before a lift can be detected; for example, if a person bends such that the sagittal angle begins at a local minimum of 50 degrees, goes to a local maximum of 60 degrees, and returns to a local minimum of 50 degrees, no lift is detected, because, although the peak sagittal flexion of 60 degrees exceeds the MPH of 30 degrees, the prominence (i.e., the 10 degree difference between the 60 degree peak and the 50 degree local minimum) does not exceed the 40 degrees MPP. In some embodiments, a lift may be detected, for example, when the sagittal flexion begins at a local minimum of 5 degrees, goes to a local maximum of 60 degrees, and returns to a local minimum of 10 degrees; in this example, the peak of 60 degrees exceeds the MPH of 30 degrees and the difference between the local maximum and the local minimum (i.e., the 50 degree difference between the 60 degree peak and the 10 degree local minimum) exceeds the MPP of 40 degrees.

In some embodiments, operation 310 includes estimating load moment experienced by a wearer who is wearing the wearable sensor 112. Typically, exact measurement data for the weight of items lifted by a worker is not available. In some embodiments, average package weights may be assigned to specific job functions. In some embodiments, for lifts where an average package weight has not been assigned, a constant average package weight is assumed. In some embodiments, the constant average package weight is 14.5 pounds. In some embodiments, lifts are assumed to be at a constant horizontal distance from the center of the hands to the L5/S1 joint in the lower spine. In some embodiments, the constant horizontal distance is 12 inches. In some embodiments, the constant average package weight and the constant horizontal distance can be adjusted as needed. In some embodiments, load moment for a given lift is determined by multiplying the weight by the horizontal distance.

In some embodiments, operation 310 includes detection of lumbar motion by the worker. In some embodiments, because the wearable sensor 112 is worn on the chest, a constant is applied to trunk motion values measured by the wearable sensor 112 in order to evaluate lumbar motion. In some embodiments, the constant is determined based on the distance of the wearable sensor 112 above the wearer's hip relative to the length of the lumbar section of the human spine. In some embodiments, this calculation is adjustable based on the height of the individual, and assumes traditional proportions. In some embodiments, recorded lumbar motion velocities are filtered and normalized to eliminate noise prior to analysis.

In some embodiments, the distance between the wearable sensor 112 and the wearer's hip is assumed to be constant for all wearers of each gender. In some embodiments, all males are assumed to be wearing the wearable sensor 112 at the height of an average-height male, and all females are assumed to wear the wearable sensor 112 at the height of about an average-height. In some embodiments, sensor-to-hip heights are determined experimentally by measuring the comfortable as-worn position of the wearable sensor 112 on test participants and using the measured heights as a constant. In some embodiments, this method can be effectively used for users of all heights because the lumbar length is also assumed to be the 50% length for males and females for all users. In some embodiments, this is based on the assumption that both the sensor-to-hip height and the lumbar length will scale proportionally for users of different heights. In some embodiments, based on this assumption, the correlation factor of the hip to the wearable sensor 112, divided by lumbar length, is used to translate chest to lumbar motion and remains unchanged, and thus constant for all male and female users. Summarizing the above, in some embodiments, lumbar motion is calculated as trunk motion multiplied by lumbar length, divided by sensor-to-hip length.

The data analysis may quantify risk and quality of worker movements. These characterizations may be based upon one or more of industry standards, ergonomist recommendations, and combinations thereof. Examples of industry standards may include, but are not limited to, the Washington State Dept. of Labor & Industries Hazard & Caution Zone Ergonomic Checklist, RULA (Rapid Upper Limb Assessment), REBA (Rapid Entire Body Assessment), and the NIOSH lifting equation. Examples of ergonomist recommendations may include, but are not limited to, "The Role of Dynamic Three-Dimensional Trunk Motion in Occupationally-Related Low Back Disorders" by William S. Marras, 1993. Each of these industry standards and ergonomist recommendations is hereby incorporated by reference in their entirety.

For example, the Washington State Dept. of Labor & Industries Hazard & Caution Zone Ergonomic Checklist list the following hazards and corresponding times for movements occurring more than one day per week and more frequently than one week per year:

TABLE 1

Caution Zone Recommendations

Awkward Posture

Working with the hand(s) above the head, or the elbow(s) above the shoulders more than 2 hours total per day.
Working with the neck or back bent more than 30 degrees (without support and without the ability to vary posture) more than 2 hours total per day.
Squatting more than 2 hours total per day.
Kneeling more than 2 hours total per day.

High Hand Force

Pinching an unsupported object(s) weighing 2 or more pounds per hand, or pinching with a force of 4 or more pounds per hand, more than 2 hours total per day (comparable to pinching half a ream of paper)
Gripping an unsupported objects(s) weighing 10 or more pounds per hand, or gripping with a force of 10 or more pounds per hand, more than 2 hours total per day (comparable to clamping light duty automotive jumper cables onto a battery)
Repeating the same motion with the neck, shoulders, elbows, wrists, or hands (excluding keying activities) with little or no variation every few seconds, more than 2 hours total per day.
Performing intensive keying more than 4 hours total per day.

Repeated Impact

Using the hand (heel/base of palm) or knee as a hammer more than 10 times per hour, more than 2 hours total per day.

Heavy, Frequent or Awkward Lifting

Lifting object weighing more than 75 pounds once per day or more than 55 pounds more than 10 times per day.
Lifting objects weighing more than 10 pounds if done more than twice per minute, more than 2 hours total per day.
Lifting objects weighing more than 25 pounds above the shoulders, below the knees or at arm's length more than 25 times per day.

Moderate to High Hand-Arm Vibration

Using impact wrenches, carpet strippers, chain saws, percussive tools (jack hammers, scalers, riveting or chipping hammers) or other tools that typically have high vibration levels, more than 30 minutes total per day.
Using grinders, sanders, jigsaws or other hand tools that typically have moderate vibration levels more than 2 hours total per day.

Figure 18:
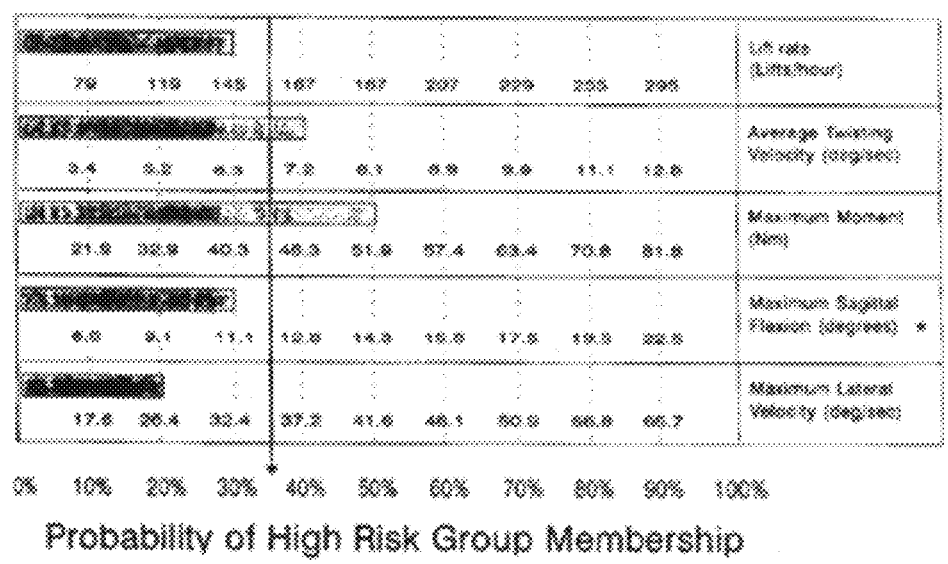
FIG. 18 is a table representing probability of membership in a high risk group based on five risk factors.

In another example, the William Marras reference provides a relationship between overall probability of high risk group membership to individual values of five risk factors. FIG. 18 shows a table illustrating this relationship.

The horizontal bars of FIG. 18 indicate measured values of each risk factor for a particular job. The average of the individual probabilities of each risk factor (horizontal axis) indicates the overall probability of high risk group membership. The risk factors indicated in FIG. 18 include lift rate (i.e., the number of lifting movements made per hour), maximum flexion (i.e., maximum sagittal flexion angle, the maximum angle of forward spine flexion in the sagittal plane over a given period of time, such as a given lift or period of lifts), average twist velocity (i.e., the average velocity of movement in the transverse or axial plane while lifting over a given period of time, such as a given lift or period of lifts), maximum movement (i.e., package weight multiplied by the horizontal distance between the hands where the load is being held and the L5/S1 joint in the spine), and maximum lateral velocity (i.e., maximum velocity of movement in the lateral plane over a given period of time, such as a given lift or period of lifts).

An example of risk factors calculated based upon measurements of the worker's movements according to FIG. 18 is performed as follows.

The five variables of lift rate (LR), maximum sagittal flexion (MF), average twist velocity (ATV), maximum moment (MM), and maximum lateral velocity (MLV) are initially calculated from the measured worker movements.

These variables are further multiplied by weighting constants (c1-c5) corresponding to each variable.

These weighted variables are summed with a further constant (c6) to yield the weighted sum Z, Equation 1:

$$Z = c_1*LR + c_2*MF + c_3*ATV + c_4*MM + c_5*MLV + c_6 \quad \text{(Eq. 1)}$$

Each of the constants $c_1$-$c_6$, are real-number values obtained from the William Marras reference.

Figure 4C:
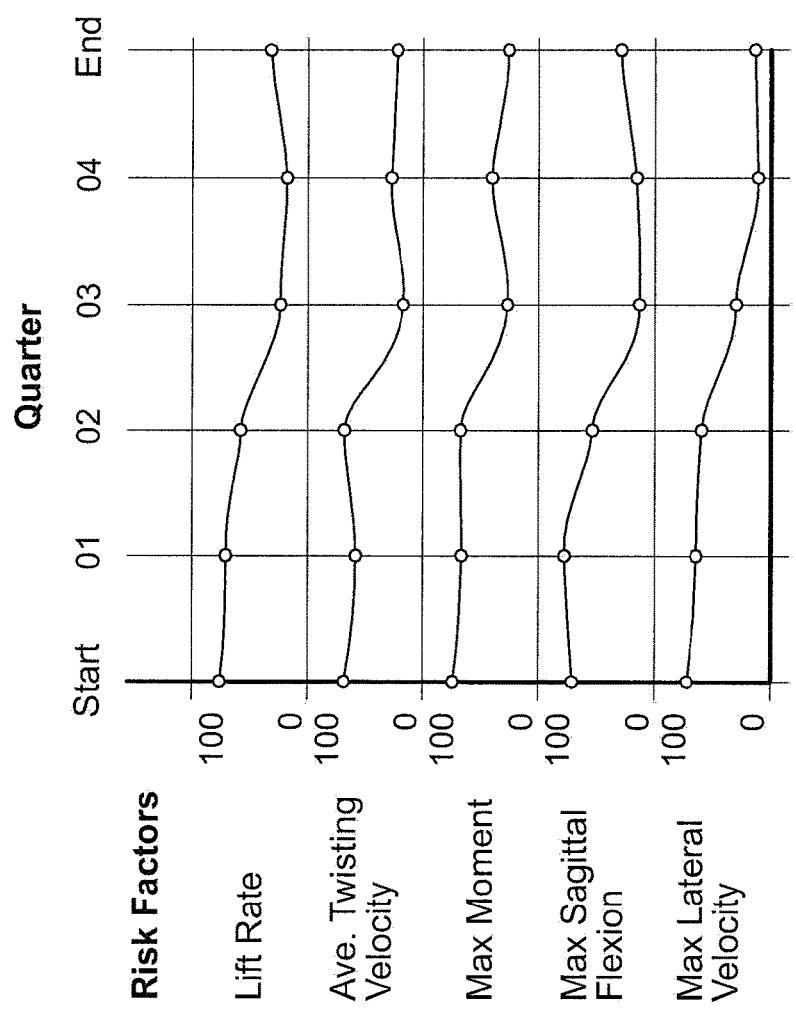
FIG. 4C is a plot illustrating calculated risk factors based upon measurements of the worker's movements according to an embodiment of the method of FIG. 3.

A logistic function is applied to the result Z to obtain the risk score, given by Equation 2 and further illustrated in FIG. 4C:

$$\text{risk score} = 1/(1+e^{-Z}) \quad \text{(Eq. 2)}$$

Figure 4D:
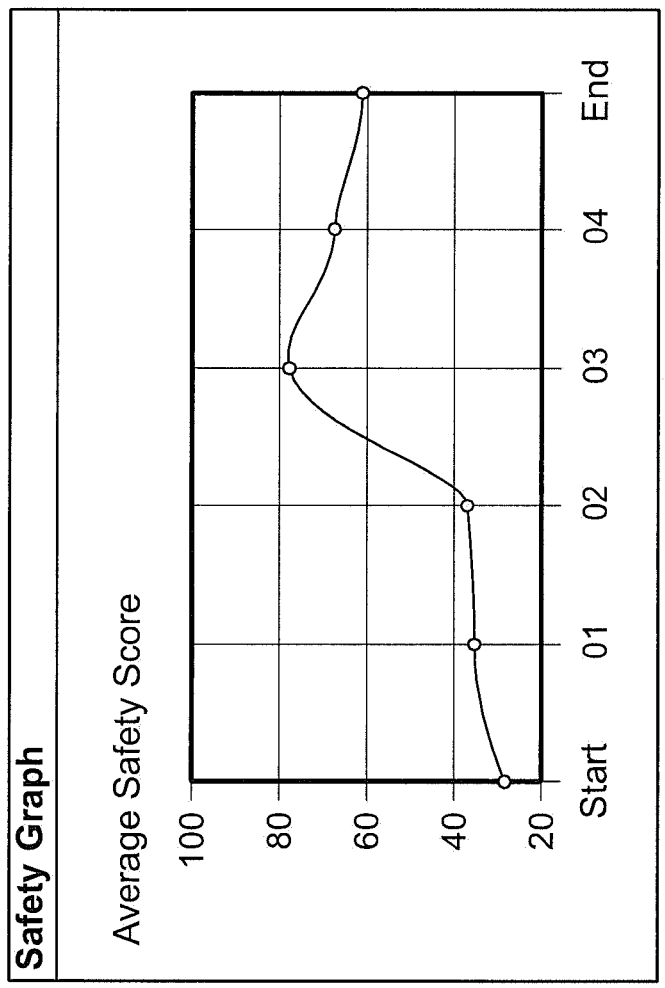
FIG. 4D is a safety graph illustrating an average safety score for a worker's movements (e.g., probability of high risk group membership) as a function of quarter, determined from the calculated risk factors illustrated in FIG. 4C.

FIG. 4D further presents a safety graph illustrating an average risk score for a worker's movements (e.g., probability of high risk group membership) as a function of time (i.e., quarter), determined from the calculated risk factors of FIG. 4C.

In some embodiments, a safety score is used rather than a risk score. In some embodiments, the safety score is the inverse of the risk score. For example, if the risk score for a given worker at a given time is 70%, the safety score for the same worker at the same time is 30%.

Figure 5A:
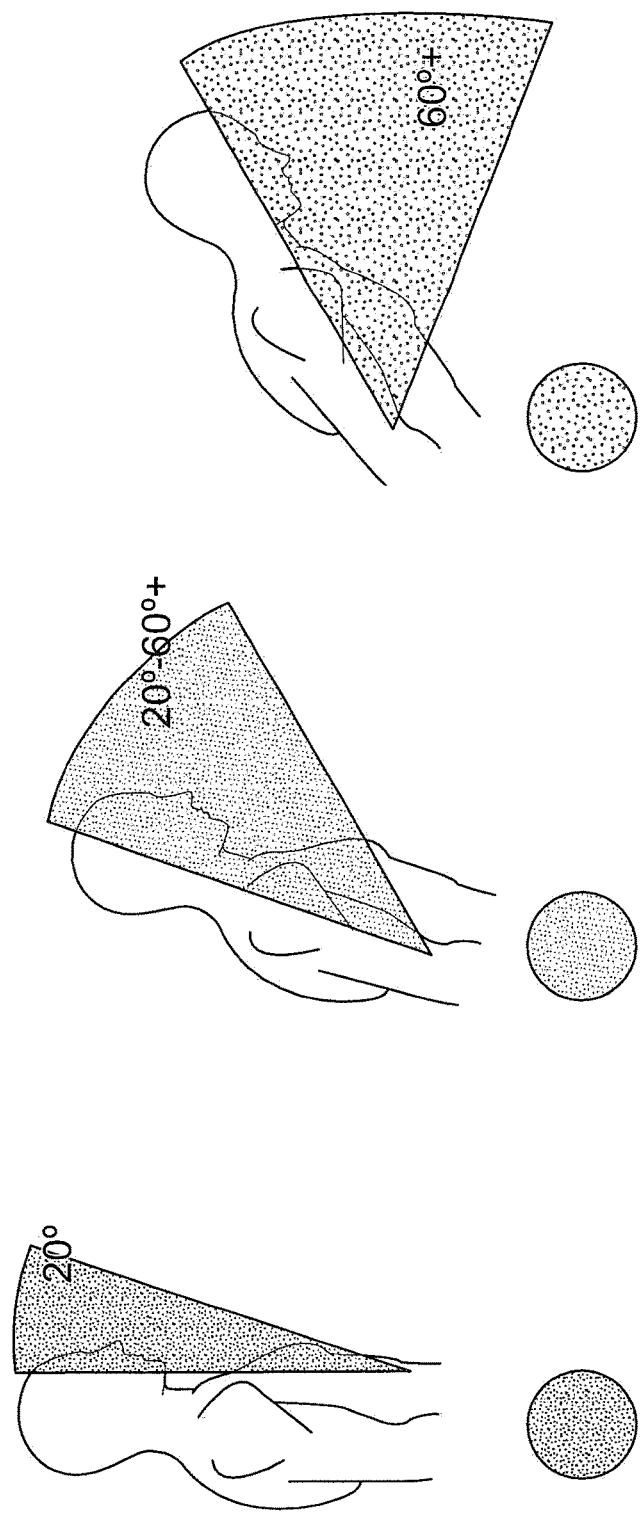
FIG. 5A is a schematic illustrations of ranges of motion of a worker.
Figure 5C:
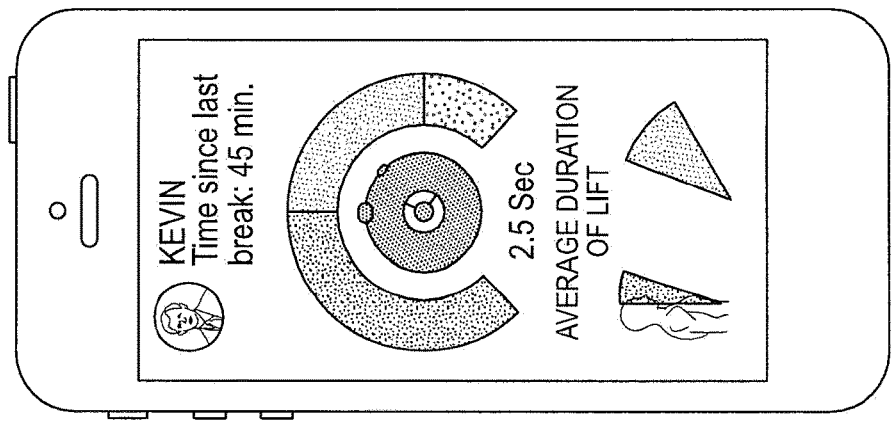
FIG. 5C is a user interface illustrating the qualitative risk assessment of FIG. 5B.
Figure 5B:
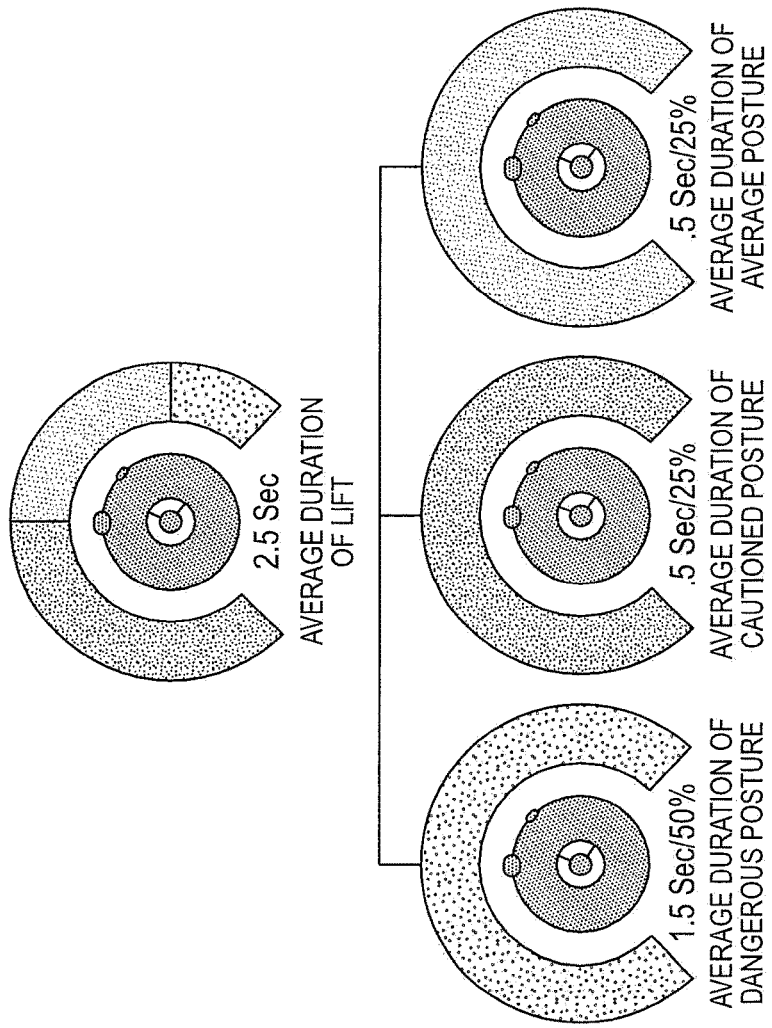
FIG. 5B is a qualitative assessment of risk corresponding to the motion ranges of FIG. 5A.

In operation 312, the analysis is displayed. In one embodiment, the analysis is presented to the individual worker whose movements have been measured. For example, in the case of lumbar flexion, angular ranges of posture motion are defined by the selected industry standards and/or ergonomist recommendations. For example, a risk assessment based upon the RULA reference is illustrated in FIG. 5A. Characterizing the measured worker movement within these ranges, combined with further measurements of the time duration over which these angles are held, may be qualitatively characterized, as average posture (low risk), cautioned posture (moderate risk), and dangerous posture (high risk) with corresponding color coded, as further illustrated in FIG. 5B. The characterization of FIG. 5B may be further displayed to a worker on his or her user computing device 104, as illustrated in FIG. 5C.

Figure 6A:
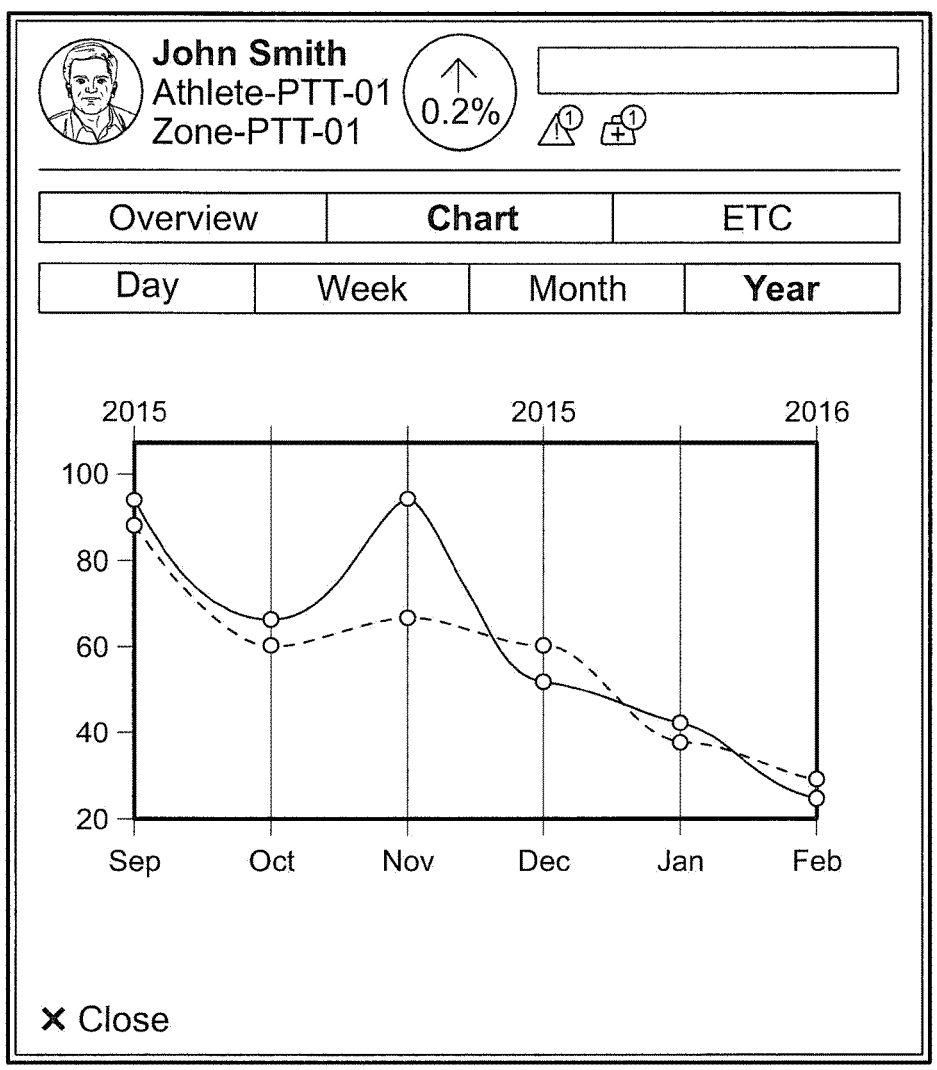
FIG. 6A is a user interface illustrating a chart of risk score as a function of time, as measured and analyzed by embodiments of the system of FIG. 1.
Figure 6B:
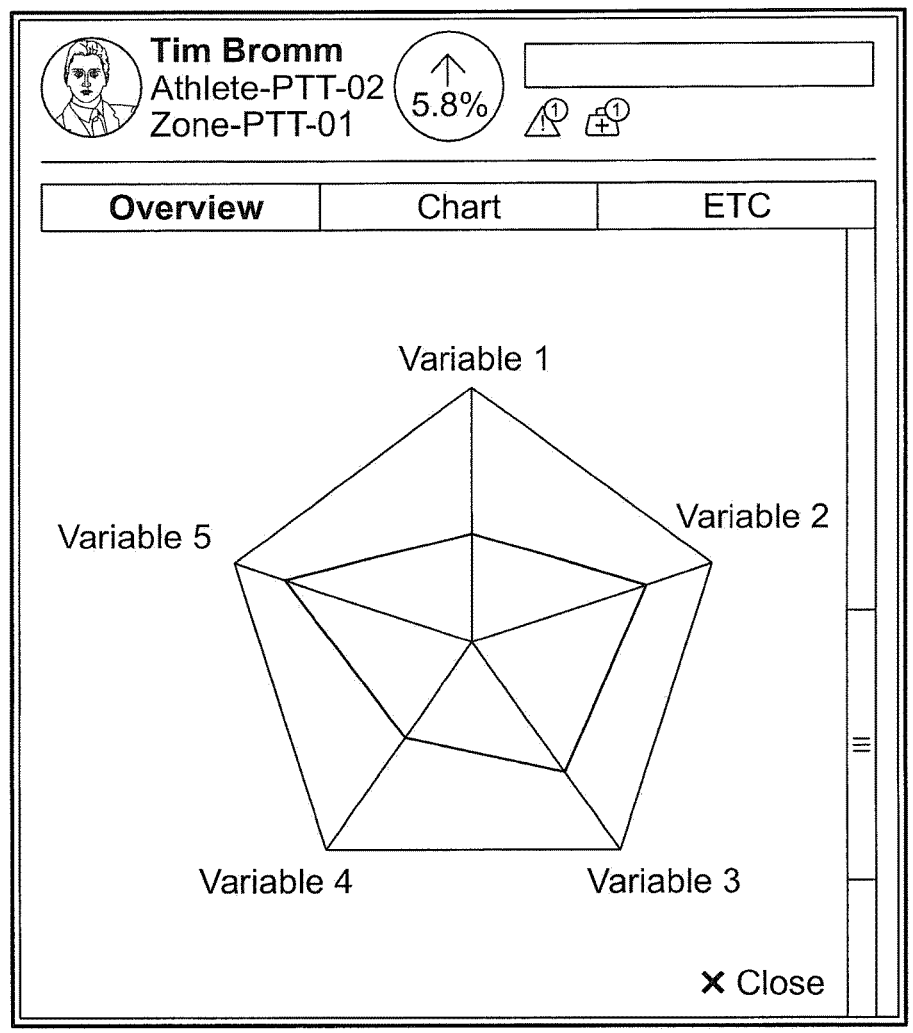
FIG. 6B is a user interface illustrating the variables of a lift, and how they can change, which in turn changes the overall risk score, as measured and analyzed by embodiments of the system of FIG. 1.

Risk scores calculated from the measured worker movements may be further displayed to the worker, as illustrated in FIGS. 6A-6C. FIG. 6A illustrates one example of how the analysis of measured worker's movements can be plotted over time and broken out into durations of time in various risk levels, in the case the various risk levels are differentiated by color. FIG. 6B illustrates risk score plotted as a function of time. FIG. 6C is a schematic illustration of the variables of a lift and how they can change, which in turn changes the overall risk score. Since the variables may change in a non-linear manner, this style of graph allows a visual of how that data looks. Some of those variables may include, but are not limited to, yaw, pitch, roll, avg. flexion, avg. twisting, etc.

Figure 7A:
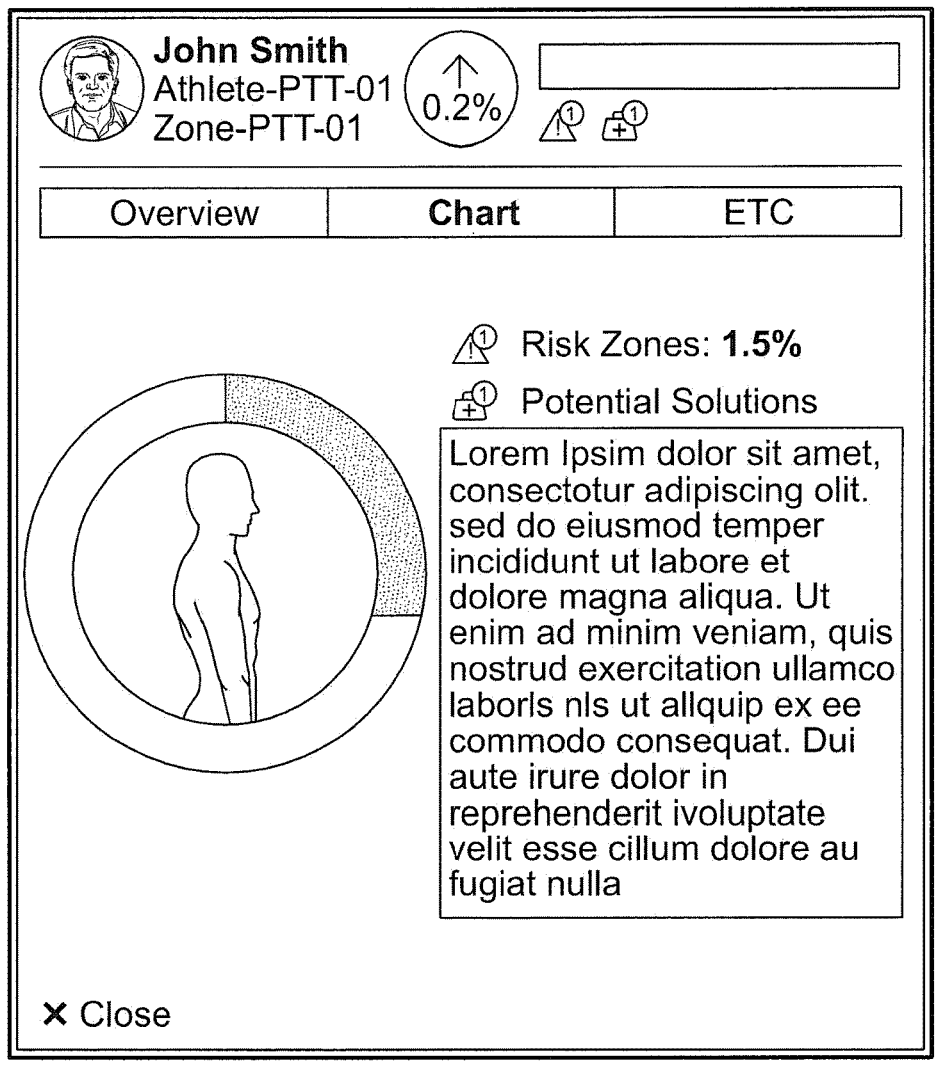
FIGS. 7A-7B are user interfaces illustrating output of a coaching component of embodiments of the system of FIG. 1.
Figure 7B:
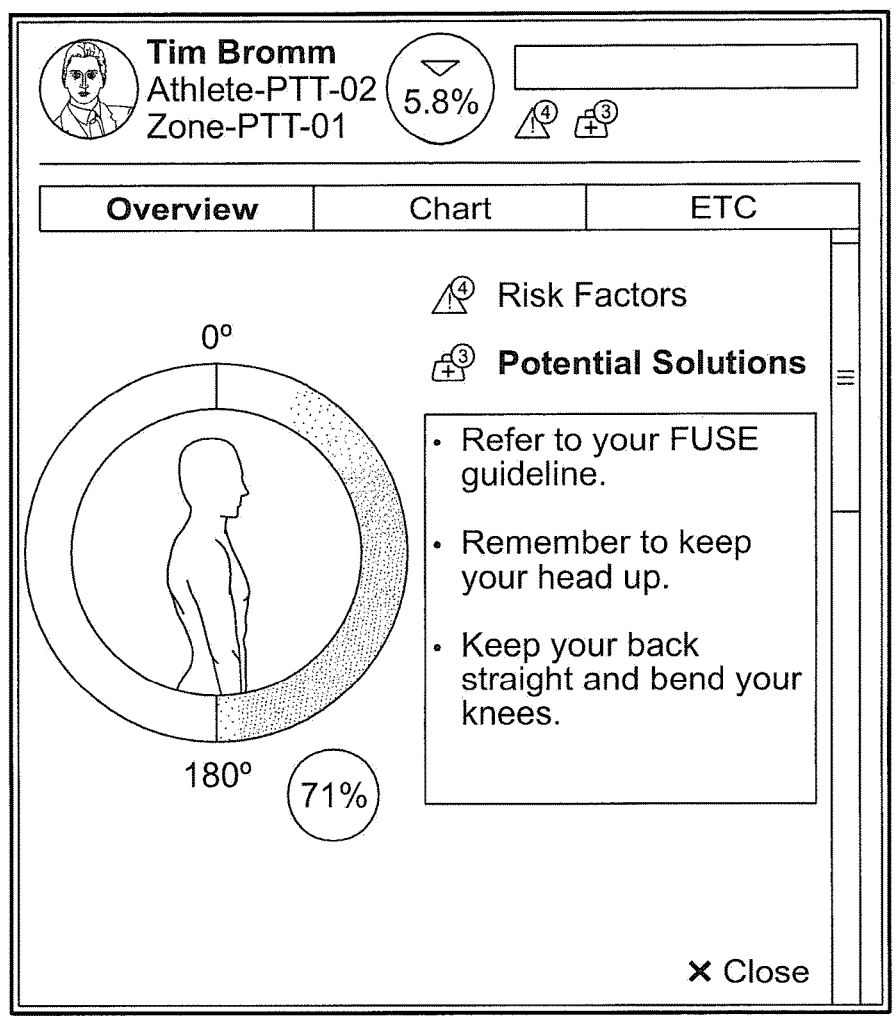

In further embodiments of operation 312, coaching interfaces generated by the coaching component 116 may be presented to the worker on his or her user computing device 104. For example, as illustrated in FIGS. 7A-7B, the worker is presented with coaching information such as risk zones and potential solutions.

Figure 8A:
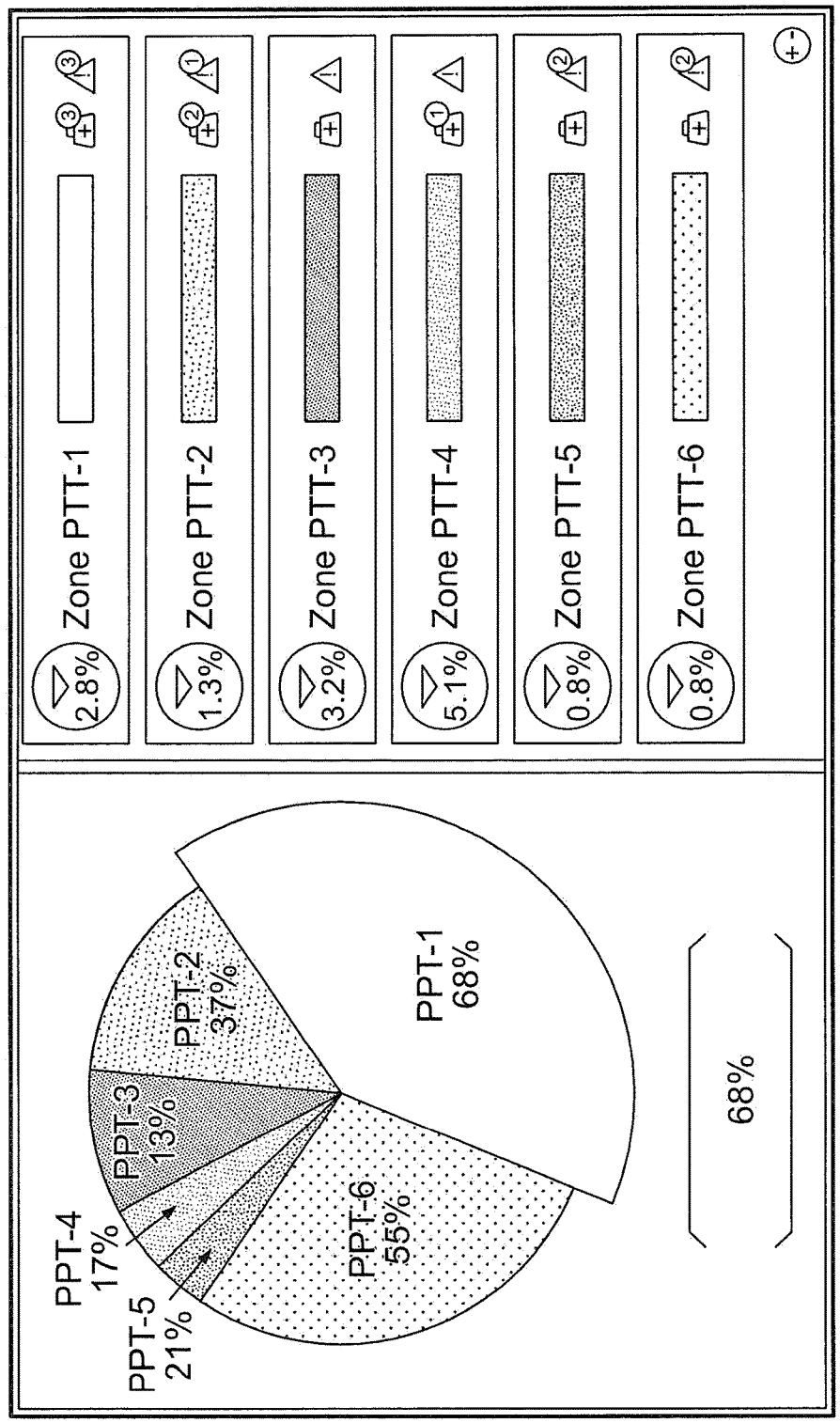
FIGS. 8A-8D are user interfaces output by a supervisor component of embodiments of the system of FIG. 1; (A) summary of worker motion risks per work zone; (B, C) summary of worker motion risks within a single zone; (D) summary of worker motion risks for a single worker.
Figure 8B:
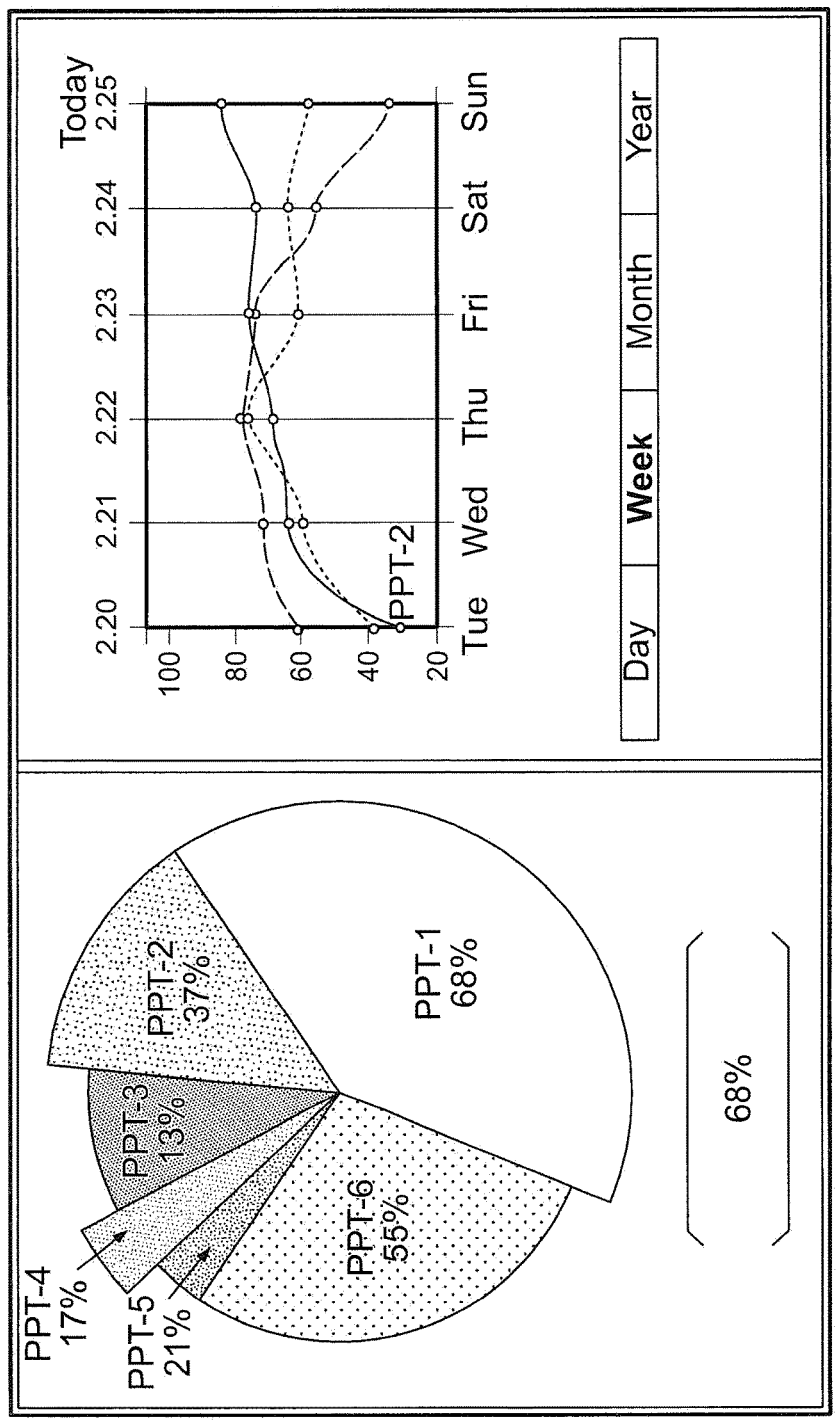
Figure 8C:
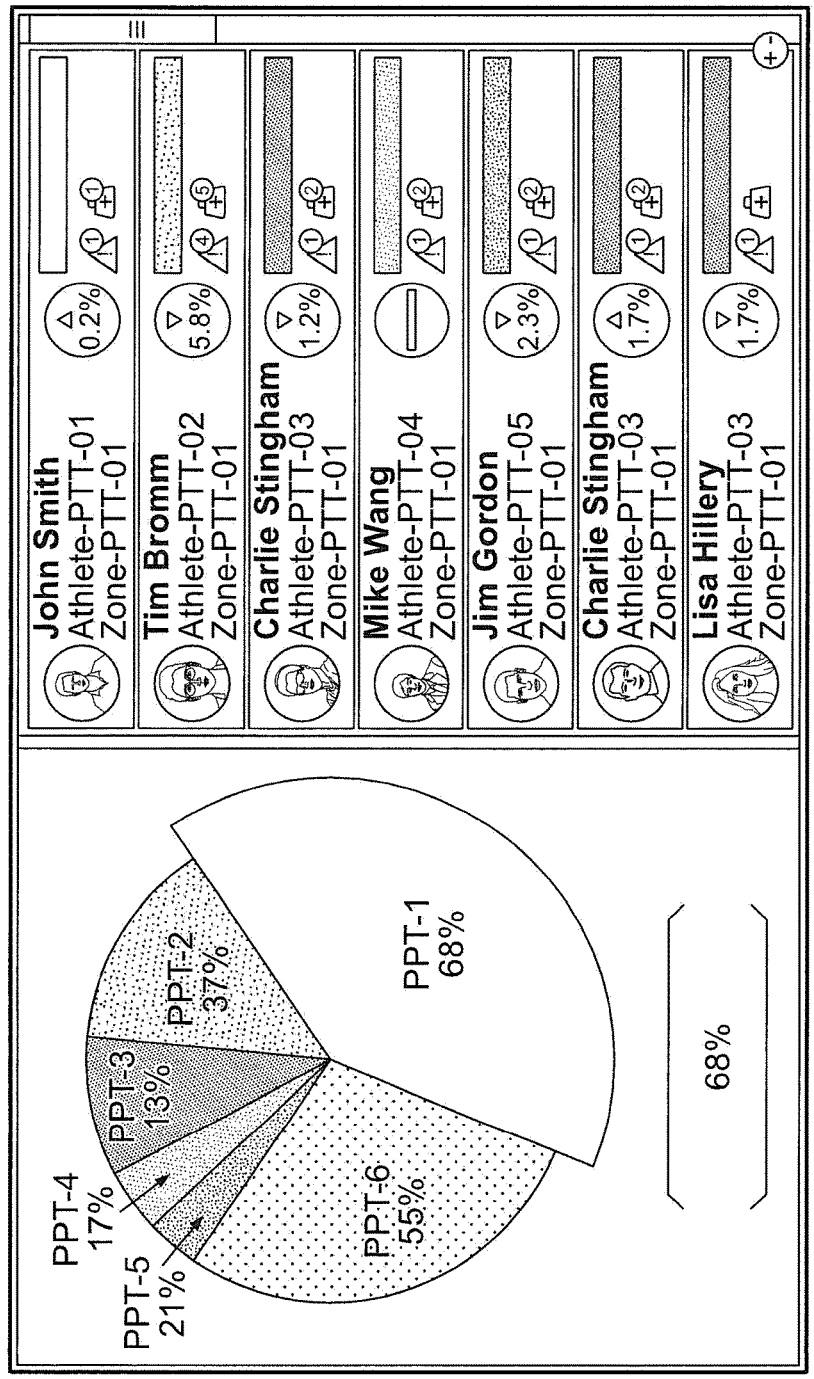
Figure 8D:
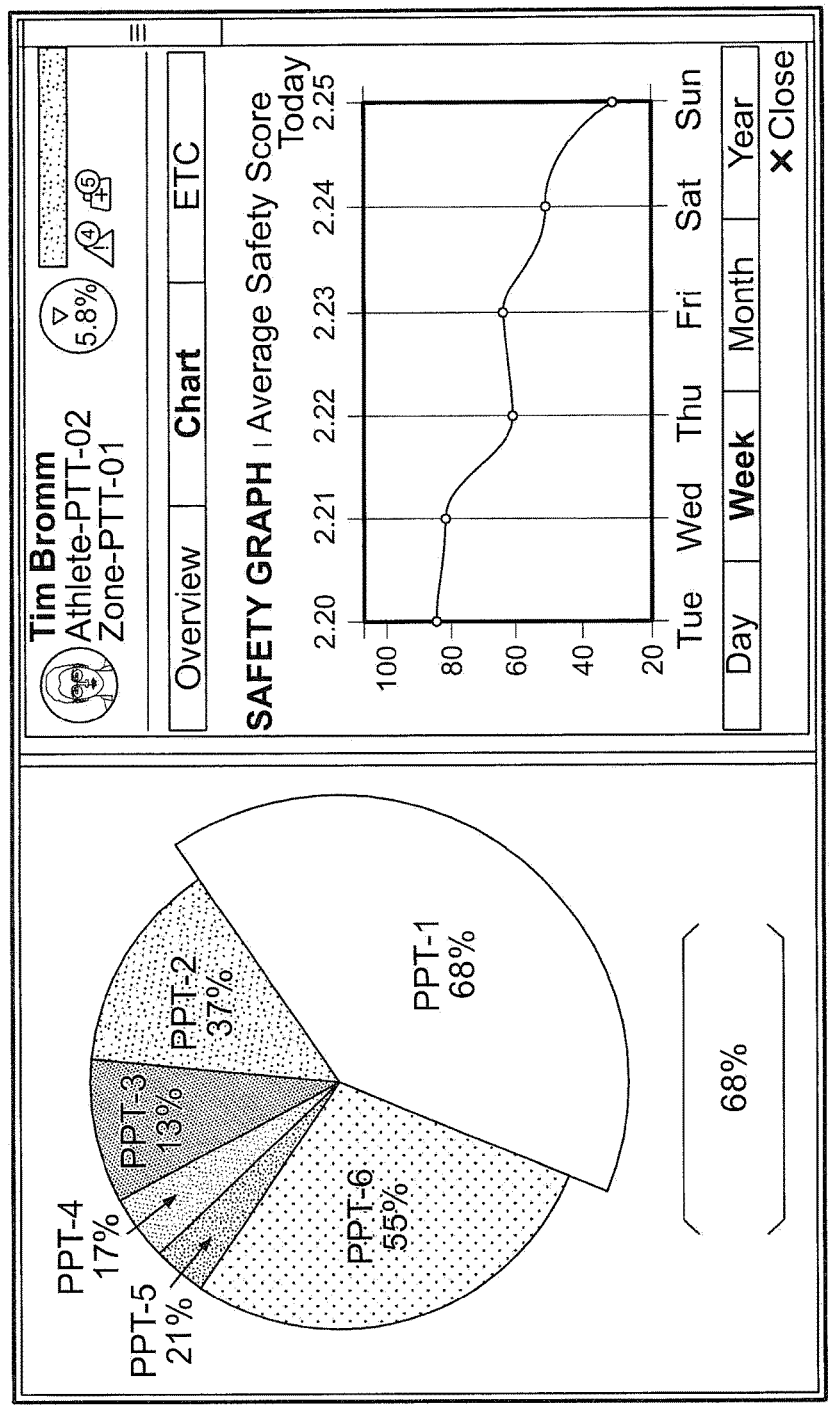

In additional embodiments of operation 312, supervisor interfaces generated by the supervisor component 120 may be presented to a supervisor on his or her user computing device 104. For example, as illustrated in FIG. 8A, the supervisor may be presented with risk scores for workers aggregated by zones or other commonalities across groups of workers, including, in some embodiments, through the use of metadata (common descriptions include, for example, palletization, depalletization, in-bound, out-bound, by city, by region, by time of day, by similar worker characteristics, by history of previous injuries, etc.). As further illustrated in FIG. 8B, the supervisor may also view risk scores for workers aggregated by zones as a function of time. In another embodiment, illustrated in FIG. 8C, the supervisor may select a specific zone and be presented with risk scores for each worker within that zone, beneficial for the purpose of comparison. In further embodiments, illustrated in FIG. 8D, the supervisor may select a specific worker within a zone and be presented with the risk score for that worker as a function of time.

In some embodiments, the activity assessment system 102 provides interventions in real time. In some embodiments, the activity assessment system 102 provides interventions directly to a worker while the worker is at work. In some embodiments, the activity assessment system 102 provides interventions immediately following a lifting event. In some embodiments, interventions take the form of either positive or negative feedback immediately following a lifting event. In some embodiments, feedback includes tactile feedback through a vibration motor of the wearable sensor 112. In some embodiments, feedback includes auditory feedback through a speaker of the wearable sensor 112. In some embodiments, feedback includes visual feedback through the display 210 or an LED of the wearable sensor 112. In some embodiments, feedback includes informing a worker that a lift that they have performed is within a safe range. In some embodiments, feedback includes informing a worker that a lift that they have performed is within an unsafe range. In some embodiments, the feedback (e.g., the type of feedback, the criteria according to which feedback is provided, etc.) is customizable. In some embodiments, the customization is based on a profile of the wearer. In some embodiments, customization is based on manager input. In some embodiments, customization is based on an algorithm. In some embodiments, the wearable sensor 112 includes a locally stored algorithm for determining when feedback is to be provided.

In some embodiments, the activity assessment system 102 uses recorded data to predict future occurrences. In some embodiments, the activity assessment system 102 determines how individuals may meet criteria about behaviors that identify individuals are performing unsafe activities or working in unsafe environments based on various factors. In some embodiments, the criteria include:

Ergonomists which identify scientifically proven damaging situations or behaviors. Such behaviors are determined using the scientific method and are properly documented and peer-reviewed before acceptance and use.

Patterns of behavior which identify individuals (a "fingerprint" of behavior identifies a user). In some embodiments, since assignment of a given one of the wearable sensor 112 to a given individual (i.e., user name "Bob" is metadata associated with captured information and previous information associated with "Bob" is used in predictive analysis to generate conditions and interventions). In some embodiments, use of such information provides a strong logical link between the captured data and the individual. In some embodiments, analysis may include "gait-matching," and data for which gait-matching is not consistent with other captured data in an individual's profile may be excluded from the individual's profile, in order to prevent improper data (such as data improperly recorded as a result of human error) from being introduced into a larger data set.

Patterns of behavior identified through the sensors or otherwise which identify, with scientifically acceptable statistical significance, that individuals will become injured based on past incidents. In some embodiments, this is informed through the use of historical data sets provided by a third party (e.g., an insurer), or by the organization that is using the activity assessment system 102. In some embodiments, this is also informed through OSHA statistics that correlate injury and motion. As a result, in some embodiments, individuals and organizations are provided with robust metrics to monitor, maintain and optimize workforces, and individuals are free to work in a safe environment and a safe and productive manner.

In some embodiments, predictions of future injury to be made by the activity sensing system 102 may be determined based on historical data sets. In some embodiments, such historical data sets should provide as much information as possible on past injuries and the circumstances surrounding them. In some embodiments, historical data sets include, but are not limited to, information about the job causing the injury (e.g., job title, job location, average package weight lifted, etc.) and as much information about the injured person as possible. FIG. 14 shows an exemplary chart of types of data that may be included in a historical data set. The chart of FIG. 14 includes data metrics that are sorted based on the resolution level of the information (e.g., at facility level, job level, or individual level). The first ten rows shown in FIG. 14 represent more significant types of data to include in a historical data set, while the remainder of the chart represents less significant types of data to include.

Although the wearable sensor 112 described above is adapted to measure a worker's activities in a manner suitable to predict and track lower back injuries, a similar approach may be taken to predict other areas of injury. These include, but are not limited to, hearing injury (e.g., through decibel sensors), physical impact harm (e.g., though location sensors based on various location tracking technologies), dexterous injures (e.g., through glove sensors), head injury (e.g., through hard-hat sensors), and respiratory injury (e.g., through air quality sensors).

In some embodiments, the activity sensing system 102 provides interventions other than in real time. In some embodiments, information is collated and presented to a website (for example, in real-time, in near-real-time, or at a predetermined availability schedule) where a customer's user (e.g., a worker or a manager) is permitted to review the analyzed data. In some embodiments, the information is presented in a fashion where the customer can explore the time series data on their own time, with expertise provided by the analysis engine. In some embodiments, the customer may make modifications to how they or their employees behave, intervening to make positive changes in the behavior of themselves or others. In some embodiments, access to various data, including, but not limited to, the ability to export files, to access charts, and to access aggregation and grouping options, is controlled through the use of system permissions based on roles within an organization.

In some embodiments, interventions begin with mechanical interventions and continue with subsequent targeted interventions. In some embodiments, interventions include tangible feedback. In some embodiments, interventions include haptic feedback provided through any suitable device (e.g., the wearable sensor 112 or another mobile device linked with an individual user, a heads-up display worn by an individual, a watch unit worn by an individual, a ring unit worn by an individual, etc.). In some embodiments, subsequent interventions include email. In some embodiments, subsequent interventions include SMS. In some embodiments, subsequent interventions include physically printed messages. In some embodiments, subsequent interventions include interventions provide through any suitable type of display that can be accessed by the activity assessment system 102 (e.g., a television or computer monitor linked to the activity assessment system 102 for this purpose, the wearable sensor 112 or another mobile device linked with an individual user, a heads-up display worn by an individual, a watch unit worn by an individual, a ring unit worn by an individual, etc.). In some embodiments, the provision of such interventions creates a feedback loop for an individual, which promotes the safety goals of the individual and the organization.

As used herein, the term "tangible feedback element" refers to any suitable device, including, but not limited to, those mentioned above, that is capable of providing tangible (e.g., haptic, visible, audible, etc.) feedback to a targeted entity (e.g., an individual, a group of individuals, a manager, etc.). In some embodiments, a tangible feedback element is integrated with the wearable sensor 112. In some embodiments, a tangible feedback element provides haptic feedback. In some embodiments, a tangible feedback element includes a motor suitable for providing haptic feedback. In some embodiments, a tangible feedback element provides auditory feedback. In some embodiments, a tangible feedback element includes a speaker suitable for providing auditory feedback. In some embodiments, a tangible feedback element provides visible feedback. In some embodiments, a tangible feedback element includes a display screen suitable for providing visible feedback. In some embodiments, a tangible feedback element includes an indicator light suitable for providing visible feedback. In some embodiments, a tangible feedback element includes an LED suitable for providing visible feedback. In some embodiments, a tangible feedback element directs an individual to use safety equipment. In some embodiment, a tangible feedback element directs a manager and/or a supervisor to provide safety equipment. In some embodiments, safety equipment includes, but is not limited to, one or more of an ergoskeleton to protect against lower back injury hazards, a device suitable for providing hearing protection to protect against hearing hazards, protective footwear (e.g., steel-toed boots), a device suitable for providing eye protection (e.g., safety goggles), a hazardous materials suit, and a device suitable for providing respiratory protection (e.g., a particulate mask) to protect against air quality hazards, a cooling vest to protect against heat hazards, and a harness to protect against falling hazards. In some embodiments, an ergoskeleton is the ergoskeleton marketed by StrongArm Technologies of Brooklyn, N.Y., under the trade name FLX. In some embodiments, an ergoskeleton is the ergoskeleton marketed by StrongArm Technologies of Brooklyn, N.Y., under the trade name V22. In some embodiments, a tangible feedback element includes a device that provides training to an individual. In some embodiments, a tangible feedback element provides an individual with a visual indication of proper lifting technique. In some embodiments, a tangible feedback element provides an individual with an instruction to perform a training session. In some embodiments, a training session includes alerting an individual to the use of an improper technique (e.g., an improper lift) and requiring the individual to perform the corresponding task using proper technique (e.g., a proper lift) a certain number of times to complete the training session. In some embodiments, a tangible feedback element provides an adjustment to a further wearable device worn by an individual (e.g., by configuring the tension or compression of various elastics, cords, or materials of such a device to help reinforce, limit, or restrict certain movements).

In some embodiments, the activity assessment system 102 integrates with a human resources management system. In some embodiments, the activity assessment system 102 provides recommendations to a manager based on workers' risk scores. Interventions occur at the recommendations of StrongArm based on the safety score provided to the customer. The customer can choose to implement activities, conversations, and other which will have an impact to the industrial athlete. These management techniques provide activities which we know will provide engagement from the industrial athlete and elicit a positive response. The customer has the opportunity to request and track new interventions through the website by making changes and seeing the impact of those interventions across the organization.

In some embodiments, a tangible feedback element provides automated human resources interventions based on the risk scores of one or more workers. In some embodiments, a tangible feedback element provides automated human resources interventions via integration into a human resources management system. In some embodiments, the activity assessment system provides automated human resources interventions by issuing commands to a human resources management system. In some embodiments, a tangible feedback element provides automated human resources interventions based on a risk score threshold or standard set by an employer or other organization. In some embodiments, the automated human resources interventions include, but are not limited to, automated shift selection for one or more workers based on risk scores as evaluated in reference to a threshold, standard, or other workers' risk scores. In some embodiments, the automated human resources interventions include, but are not limited to, automated shift changes or swaps based on risk scores as evaluated in reference to a threshold, standard, or other workers' risk scores. In some embodiments, the automated human resources interventions include, but are not limited to, generating a shift schedule based on the amount and type of work planned for a specific time period (e.g., a day, a week, a month, etc.) and knowledge of the safety scores or risk scores of individuals available to work during the time period. In some embodiments, the automated human resources intervention include, but are not limited to, determining a number of individuals that are needed in a facility for a specific shift, specific tasks, and/or specific job functions.

In some embodiments, a risk score or a safety score may serve as the basis for process optimizations or changes. For example, in some embodiments, risk scores or safety scores may be used to reallocate individuals to different job tasks.

For example, if an individual has performed "task A" and "task B" and has achieved better risk scores or safety scores while performing "task A" than while performing "task B," the individual may be reassigned from "task B" to "task A". In some embodiments, such interventions may provide better employee engagement and retention to companies, as workers often quit due to a mismatched skill set to job function.

In some embodiments, if a group of individuals are performing the same task or role and a specific one of the individuals has a safety score or a risk score that is better than the remainder of the group, an intervention may be triggered that can facilitate training (for example, directing the remainder of the group to observe the specific one of the individuals performing the task, creating a record of the performance of the specific one of the individuals for subsequent use to train the remainder of the group, etc.). In some embodiments, the movements of the specific individual during the task or role are categorized and a training algorithm is created using machine learning to determine all of their movements. In some embodiments, such a training algorithm can be used to facilitate understanding of when other people in the group who are performing the same task or role are doing it in a similar way or not, and to provide feedback (e.g., tangible feedback, as discussed herein) when they are not. In some embodiments, the movements of the specific individual serve as the basis for an animation that may be provided to the other individuals in the group to facilitate training.

In some embodiments, a risk score or a safety score may be used to provide underwriting insights to insurers and/or to insured organizations so that they can better assess and mitigate risk.

In some embodiments, a risk score or a safety score may be used to identify how changing certain variables (e.g., number of workers per shift, use of new equipment, use of new processes, increase in package weight, decrease in package weight, implementation or change of productivity requirements) affect the risk score or safety score, as well as the financial impact that such a change may have. In some embodiments, based on a calculated risk score or a calculated safety score, changes to such variables may automatically be triggered (e.g., a human resources management system may be instructed to change a number of workers per shift, new equipment may be provided, package weights may be increased or decreased, etc.) and what kind of financial impact it can have. In some embodiments, an activity assessment system 102 provides a tool for linking an organization's financial, operational, and safety data, which organizations may previously lack.

Figure 11A:
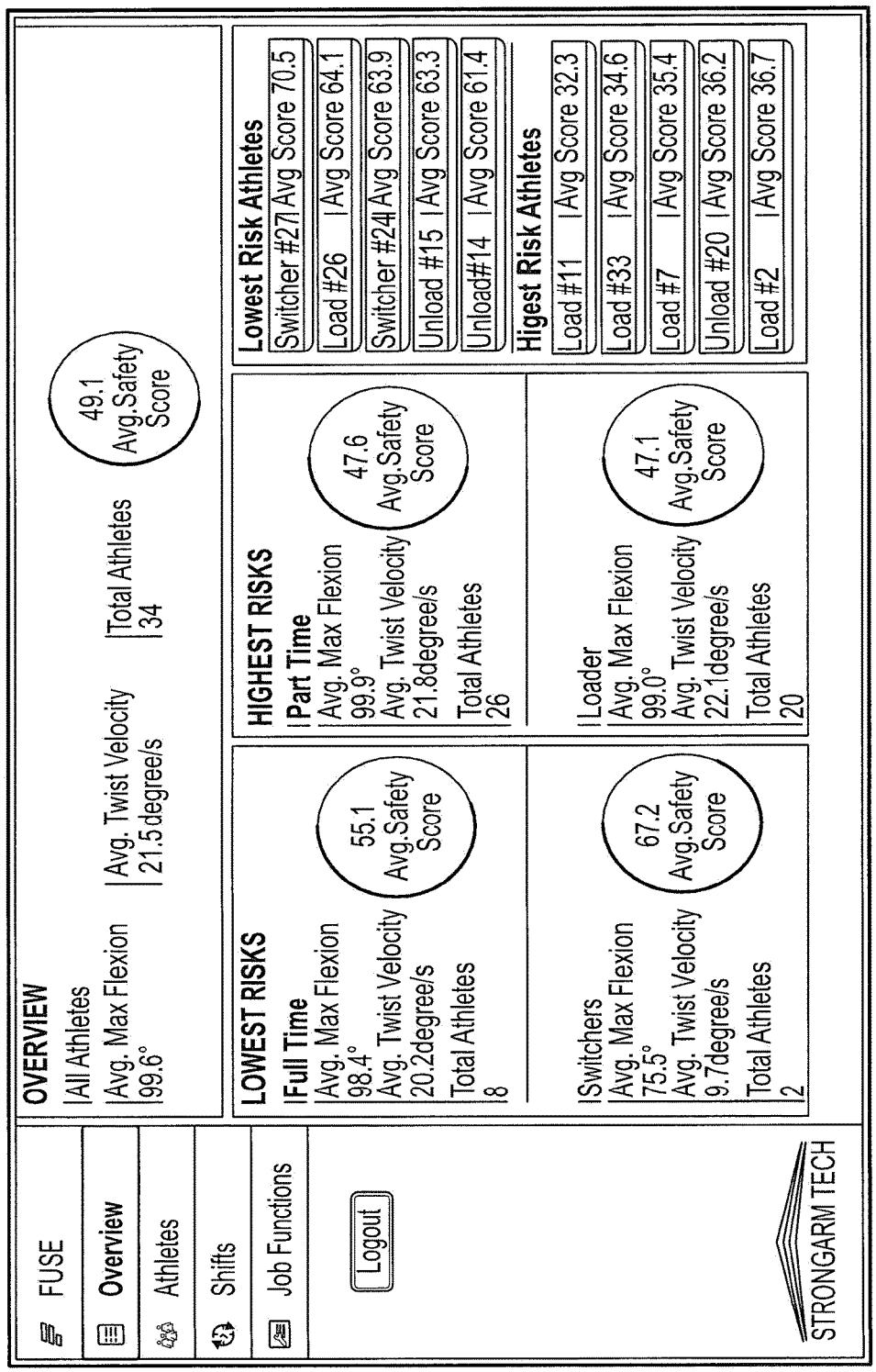
FIG. 11A is an exemplary overview display providing a summary of safety scores.
Figure 11B:
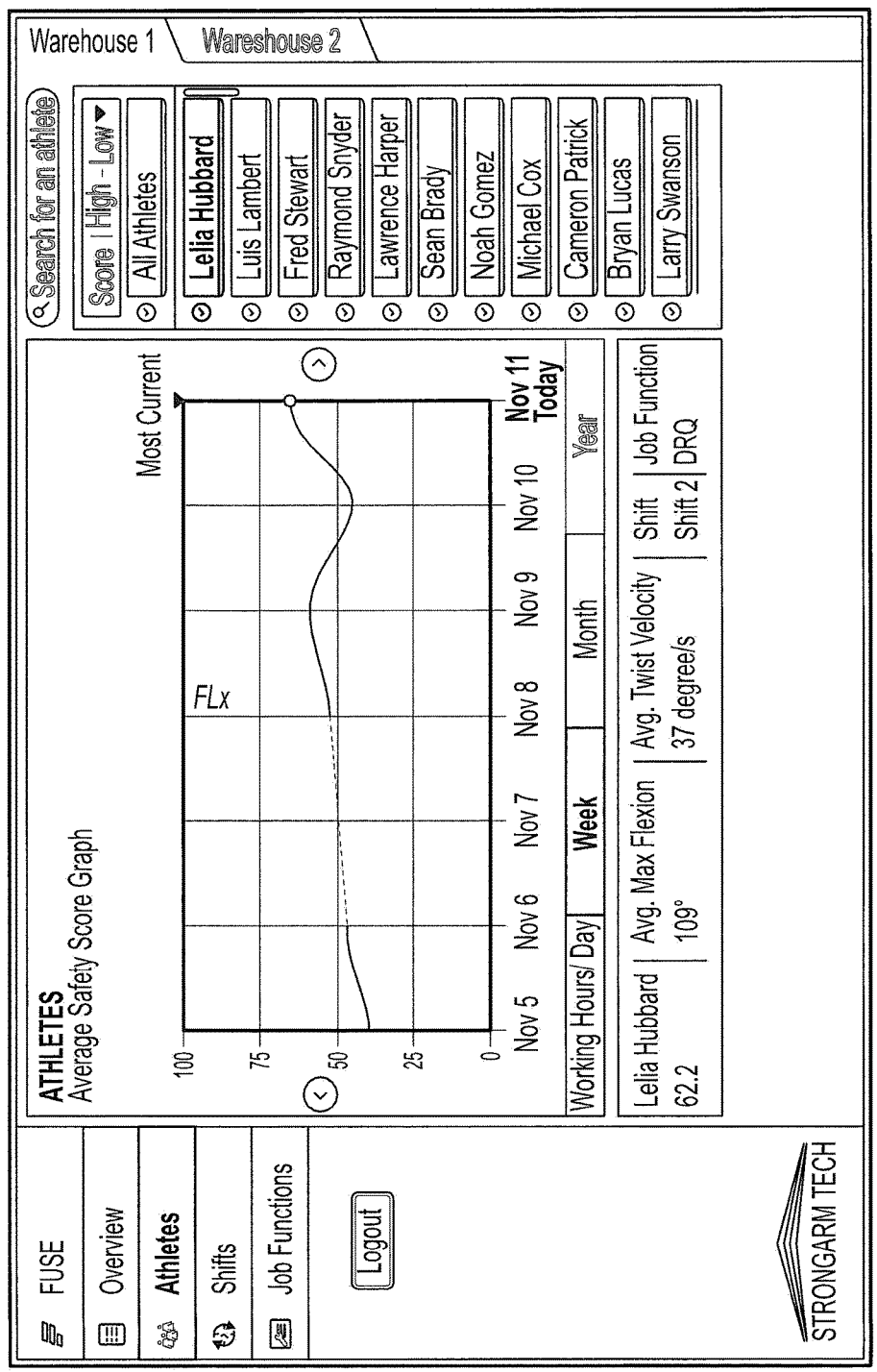
FIG. 11B is an exemplary display providing historical safety score data for an individual.
Figure 11C:
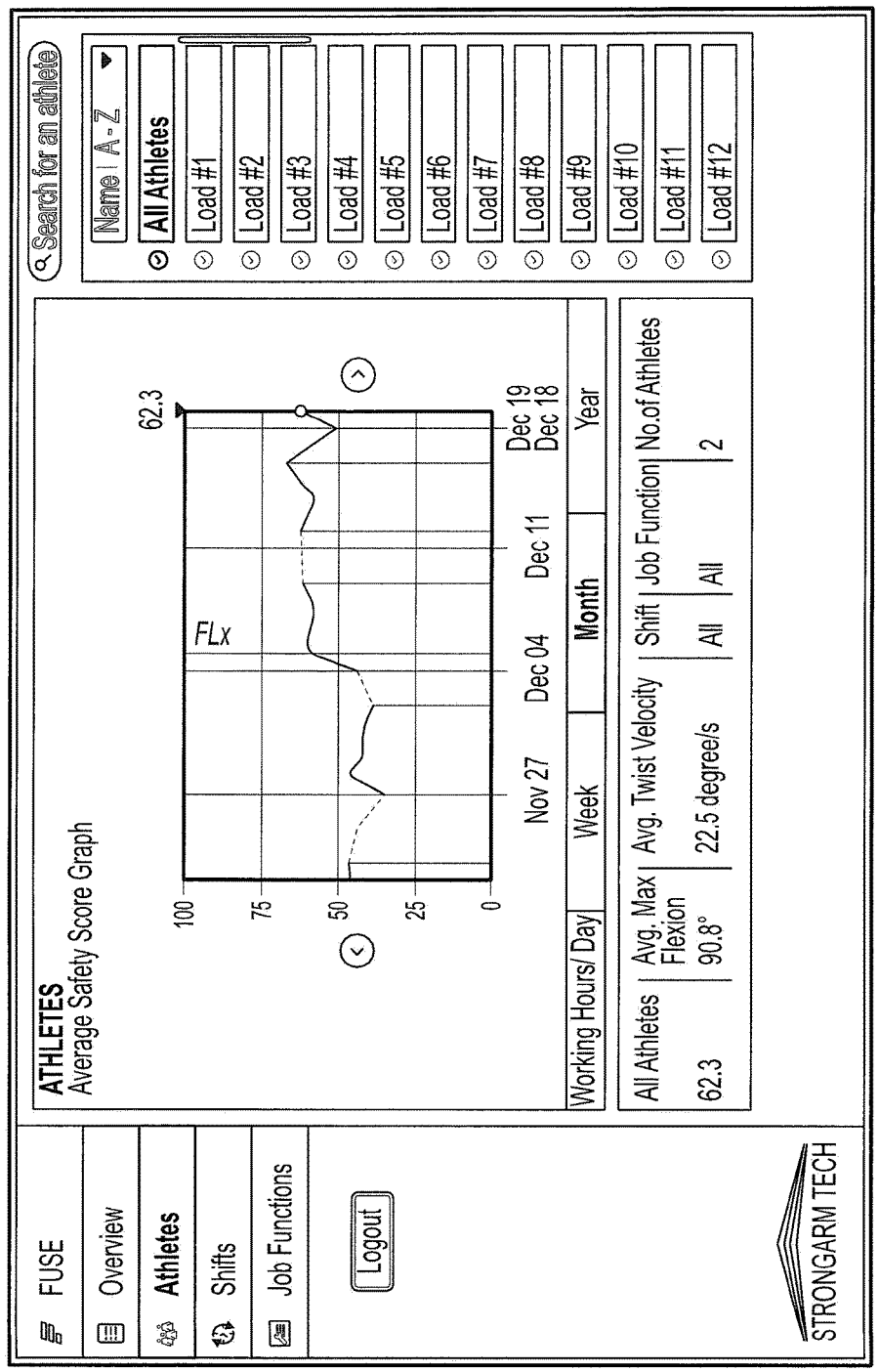
FIG. 11C is an exemplary display providing historical safety score data for a group of individuals.
Figure 11D:
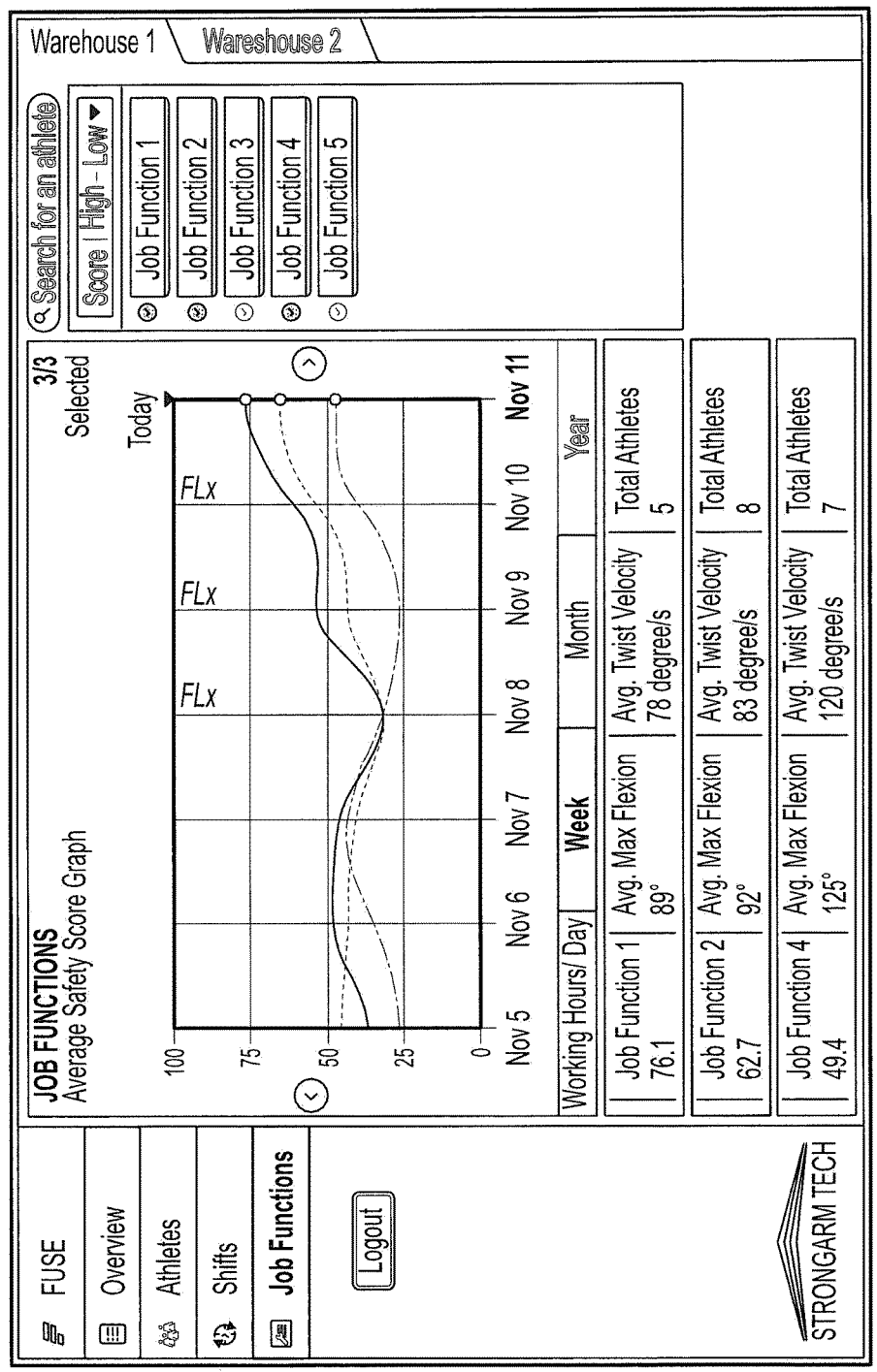
FIG. 11D is an exemplary display providing historical safety score data for a group of individuals as classified by job functions.
Figure 11E:
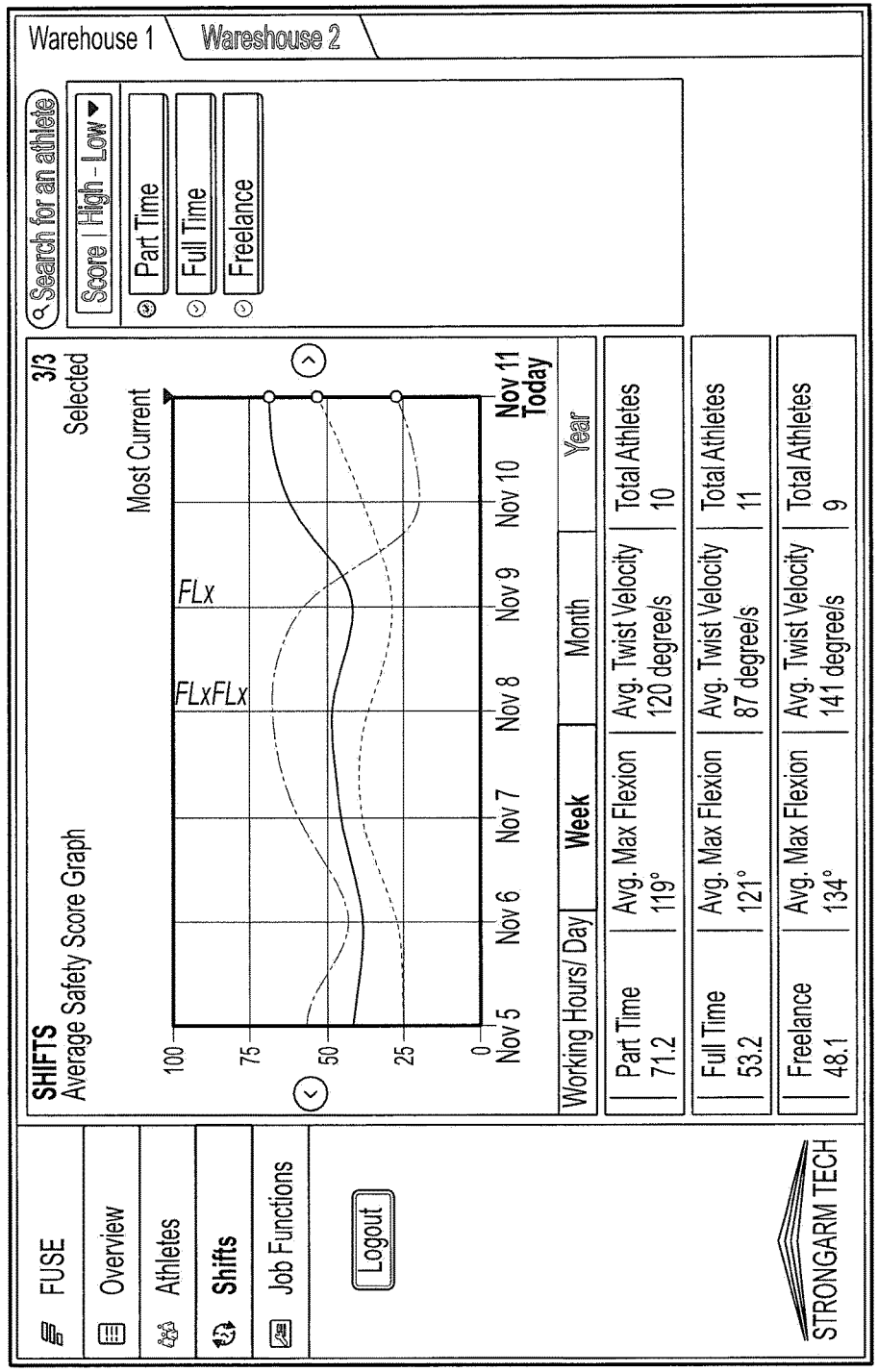
FIG. 11E is an exemplary display providing historical safety score data for a group of individuals as classified by shifts.

Referring now to FIGS. 11A through 11D, a sequence of informational displays that may be generated by the activity assessment system 102 is shown. FIG. 11A shows an exemplary overview display providing a summary of safety scores for various individuals. In the display of FIG. 11A, an overall average safety score is provided along with a summary of groups of individuals having the best and worst safety scores. FIG. 11B shows an exemplary display providing historical safety score data for a selected individual. FIG. 11C shows an exemplary display providing historical safety score data for a selected group of individuals. FIG. 11D shows an exemplary display providing historical safety score data for a group of individuals as classified by job functions. FIG. 11E shows an exemplary display providing historical safety score data for a group of individuals as classified by shifts (for example, part time, full time, and freelance).

Figure 12A:
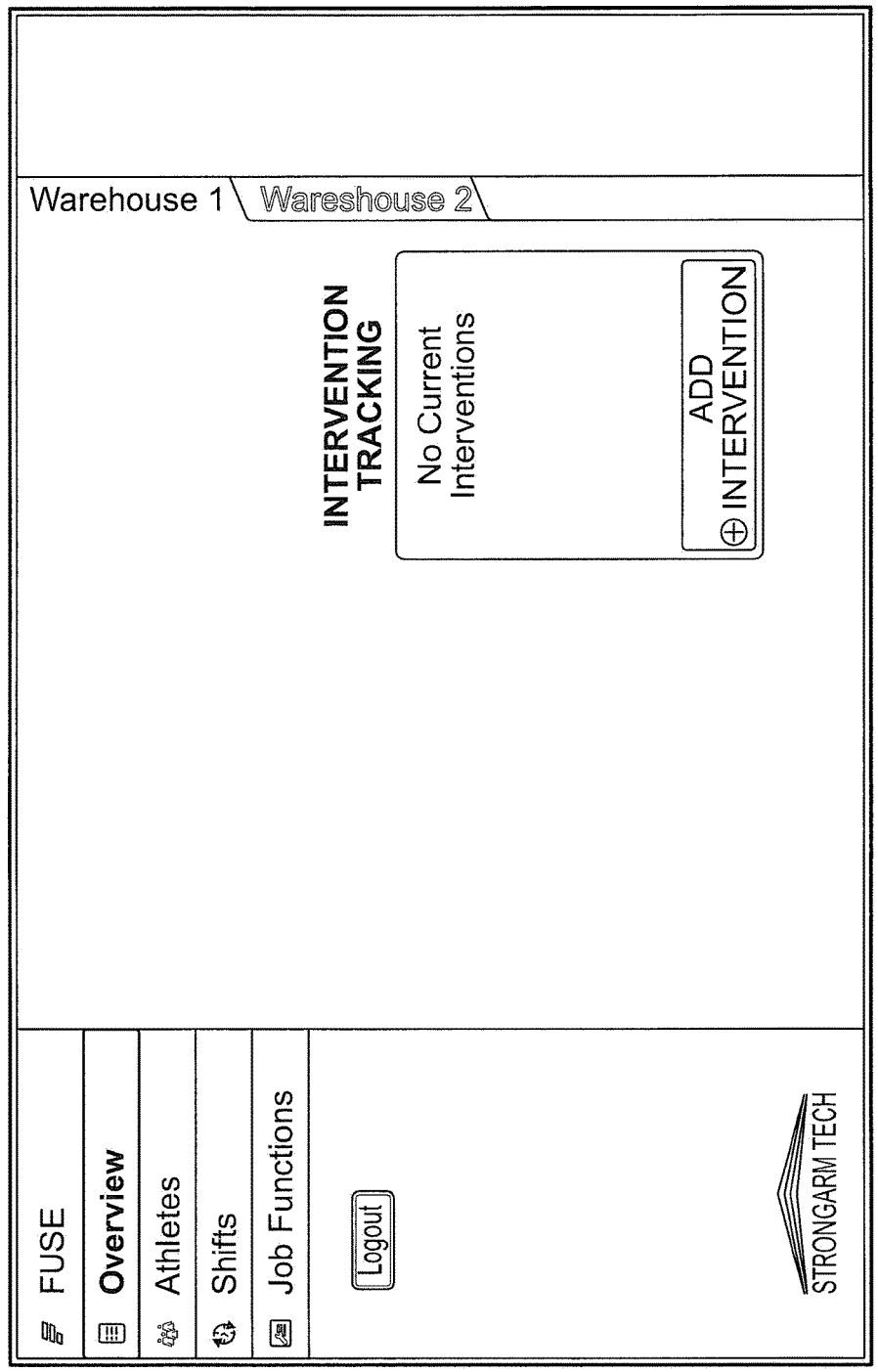
FIG. 12A is an exemplary display providing access to safety interventions.
Figure 12B:
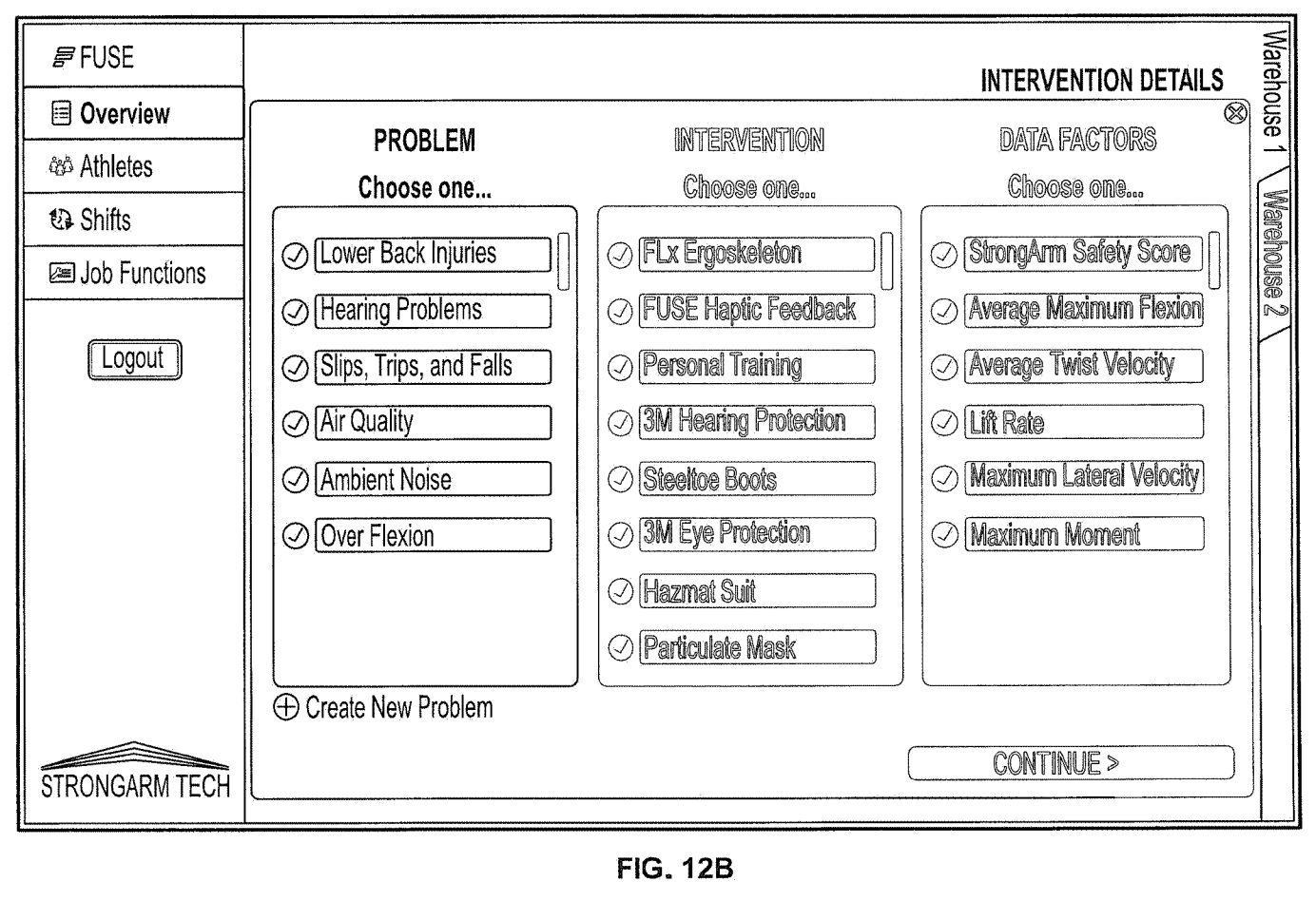
Figure 12C:
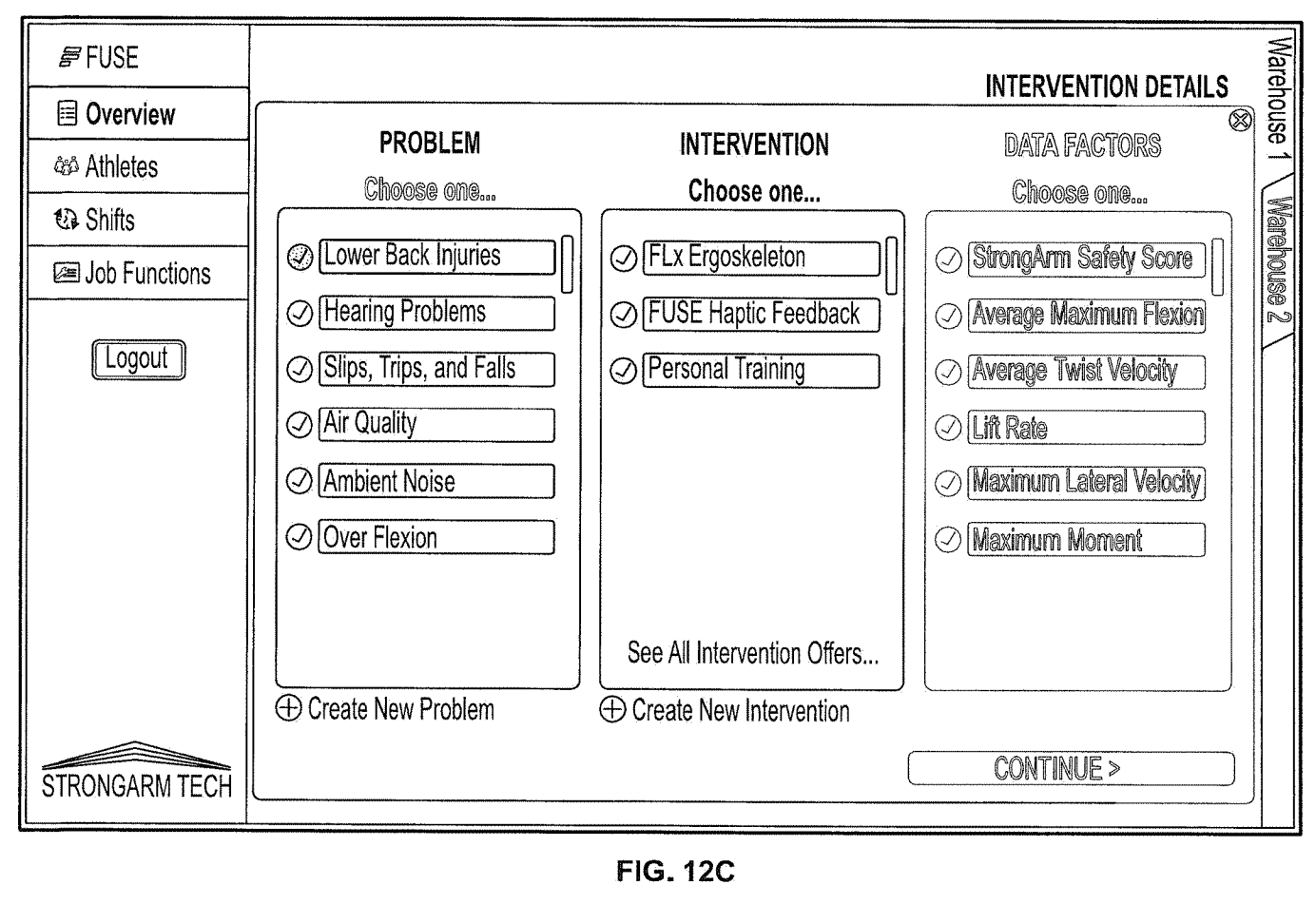
Figure 12E:
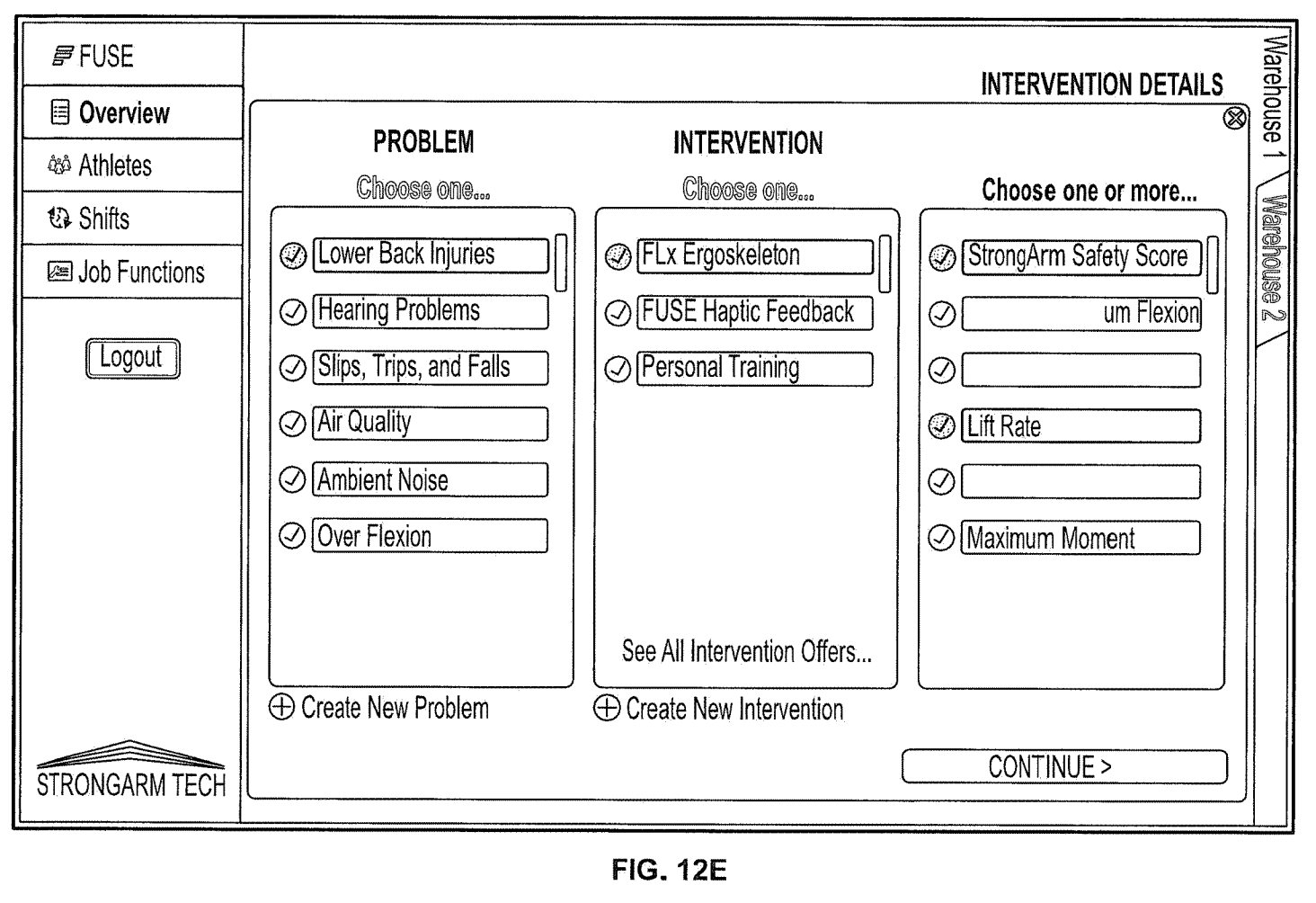
Figure 12F:
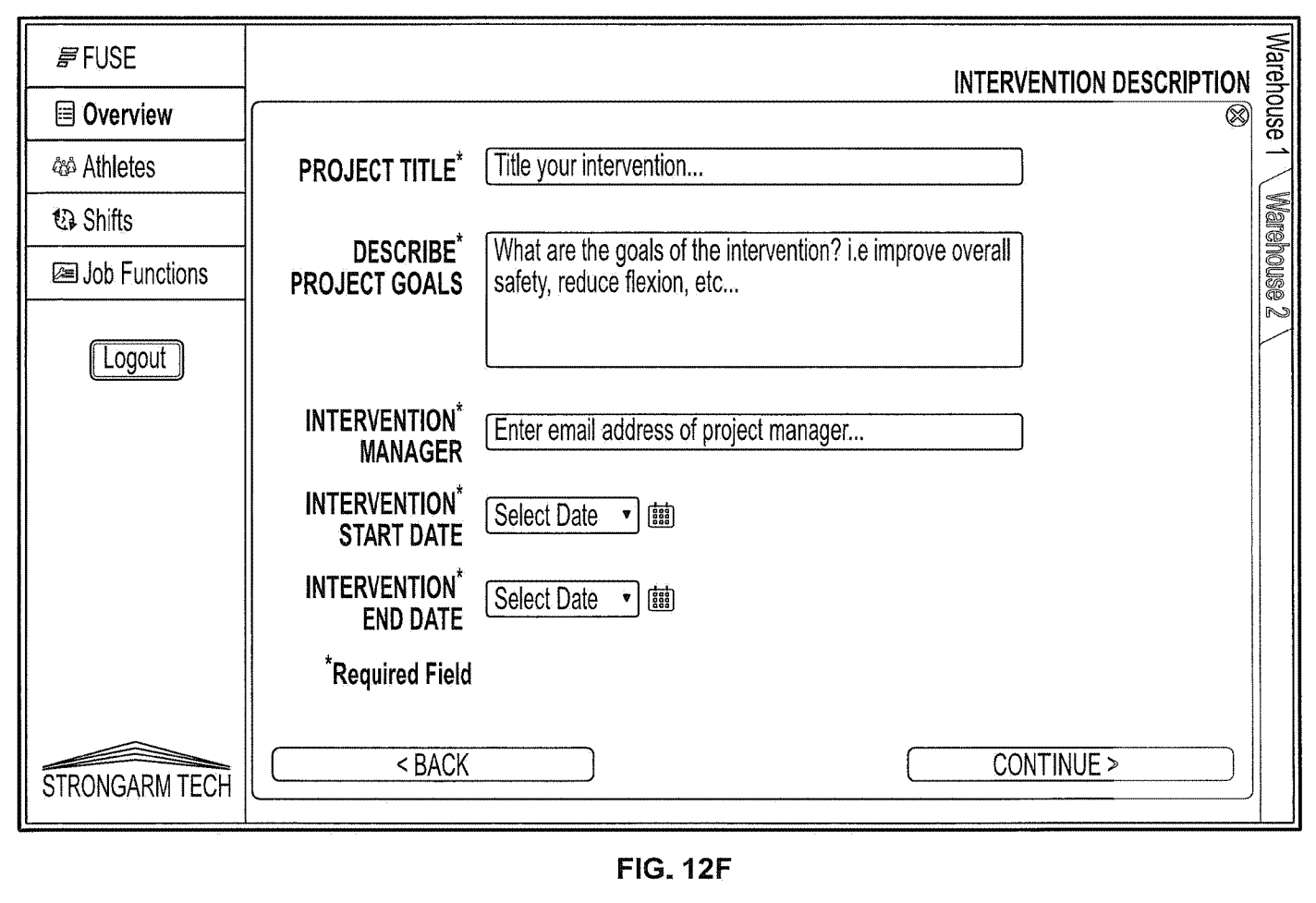

Referring now to FIGS. 12A through 12L, a sequence of displays relating to safety interventions that may be generated by the activity assessment system 102 is shown. FIG. 12A shows an exemplary display providing access to safety interventions. In the display of FIG. 12A, a prompt is provided allowing a user to add new interventions and track existing interventions. FIG. 12B shows an exemplary display providing access to configure interventions that may be triggered based on a variety of problems. In the display of FIG. 12B, interventions may be configured to address lower back injuries; hearing problems; slips, trips, and falls; air quality; ambient noise; and over flexion. FIG. 12C shows an exemplary display providing access to various interventions that may be triggered for a selected problem (e.g., a problem selected using the display shown in FIG. 12B). In the display of FIG. 12C, the interventions include use of an ergoskeleton (e.g., the use of an ergoskeleton marketed by StrongArm Technologies of Brooklyn, N.Y., under the trade name FLX); providing haptic feedback by the wearable sensor 112; providing personal training; providing hearing protection; providing steel toed boots; providing eye protection; providing a hazmat suit; and providing a particulate mask. FIG. 12D shows an exemplary display providing access to various data factors that may be evaluated in triggering a selected intervention for a selected problem (e.g., an intervention selected using the display shown in FIG. 12C and a problem selected using the display shown in FIG. 12B). In the display of FIG. 12D, data factors include a safety score calculated as described herein, an average maximum flexion, an average twist velocity, a lift rate, a maximum lateral velocity, and a maximum moment. FIG. 12E shows an exemplary display indicating a selected problem (e.g., a problem selected using the display shown in FIG. 12B), a selected intervention that may be triggered for the problem (e.g., an intervention selected using the display shown in FIG. 12C), and selected data factors that may be evaluated in triggering the selected intervention for the selected problem (e.g., data factors selected using the display shown in FIG. 12D). FIG. 12F shows an exemplary display allowing for input of information describing an intervention (e.g., a title, a narrative description, a project manager, a start date, an end date).

Figure 12G:
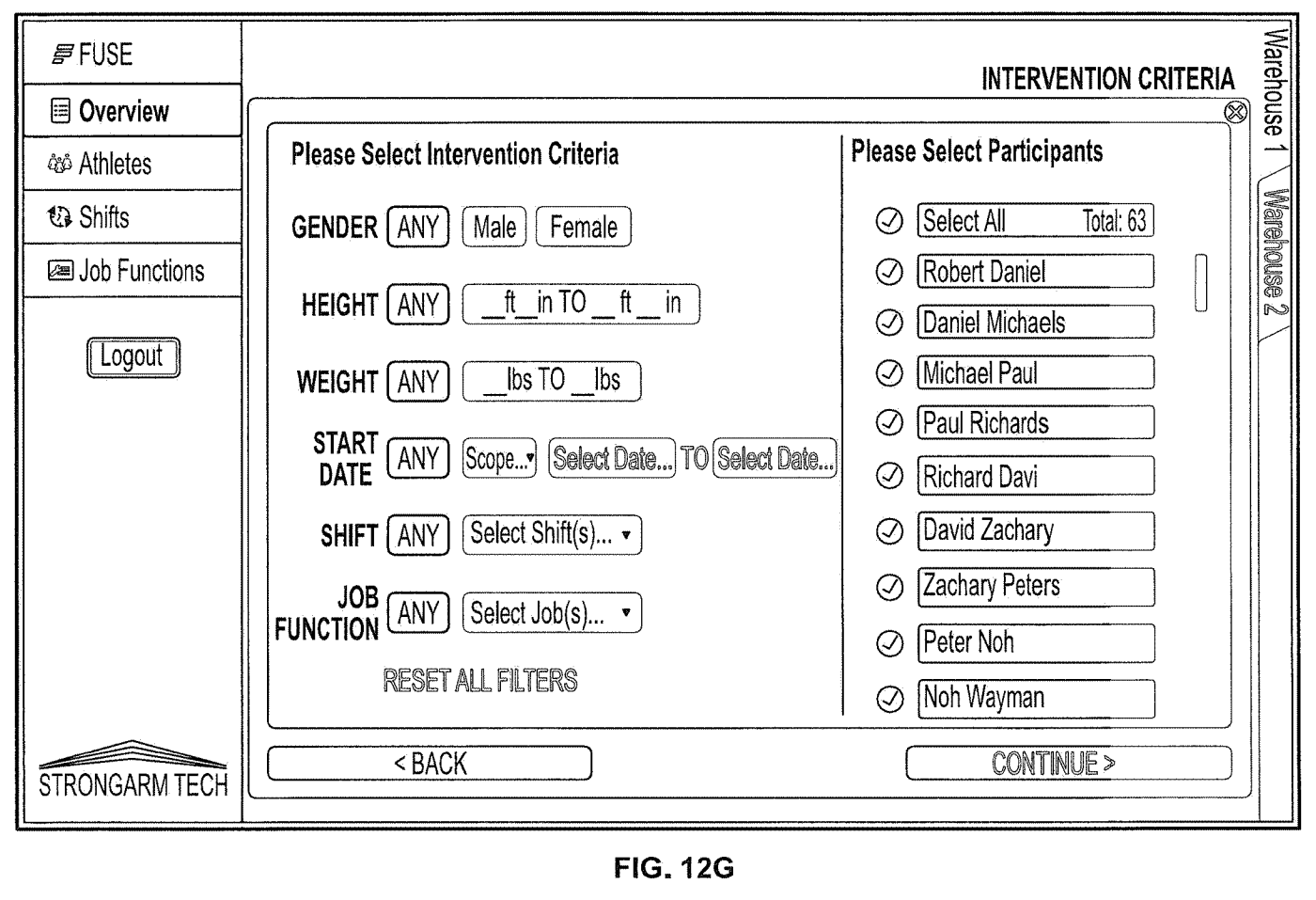
Figure 12H:
FIG. 12H is an exemplary display that that is the exemplary display of FIG. 12G after criteria have been selected.

FIG. 12G shows an exemplary display providing for selection of criteria that may be evaluated in determining whether to trigger an intervention. In the display of FIG. 12G, the criteria include gender, height, weight, start date, shift, job function, and individually named participants. FIG. 12H shows an exemplary display that results from the selection of criteria using the display of FIG. 12G. In the display of FIG. 12H, the selected criteria include gender "male," start date from Oct. 16, 2016 to Oct. 25, 2016 and job function "inbound".

Figure 12I:
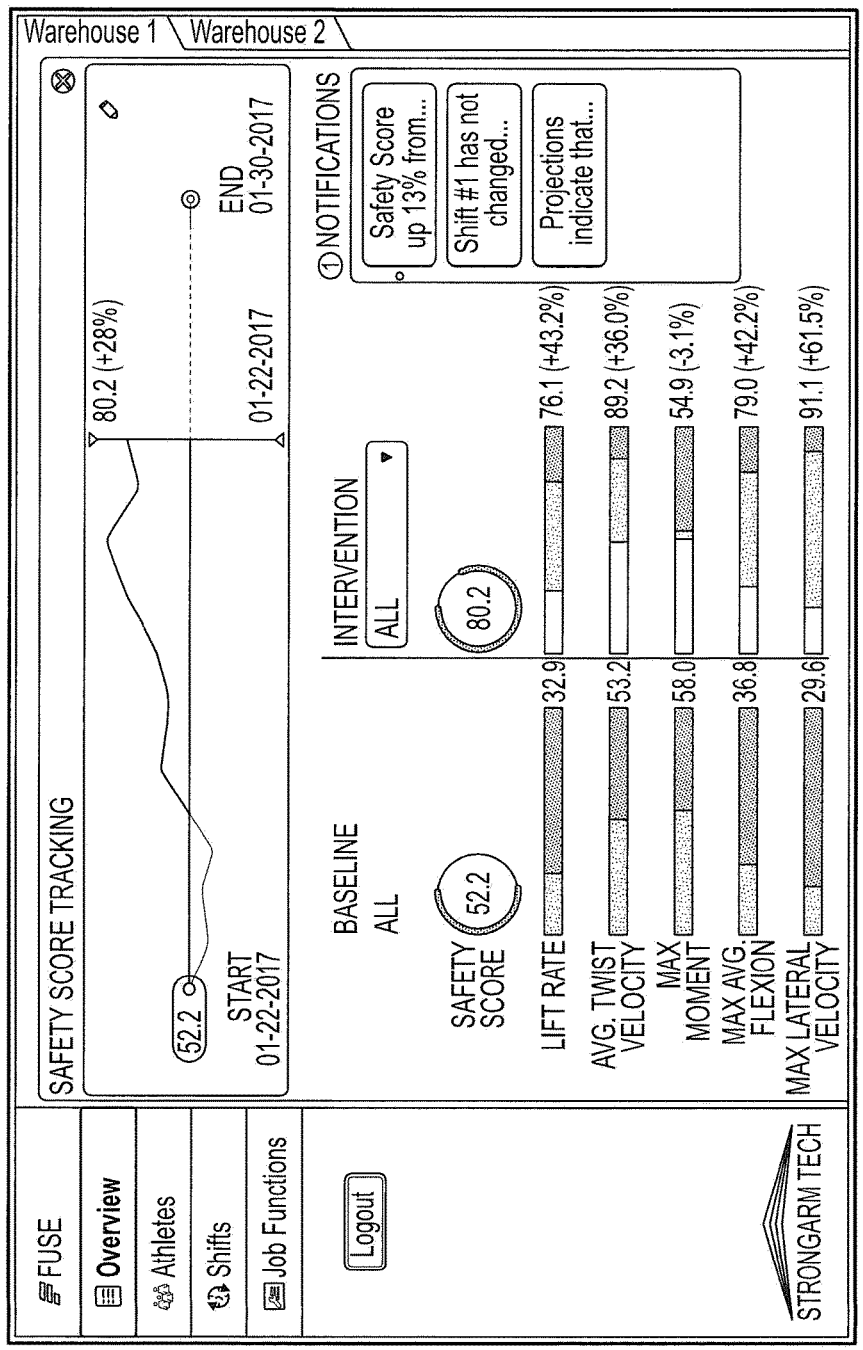
FIG. 12I is an exemplary display providing historical tracking of safety scores before and after an intervention.
Figure 12J:
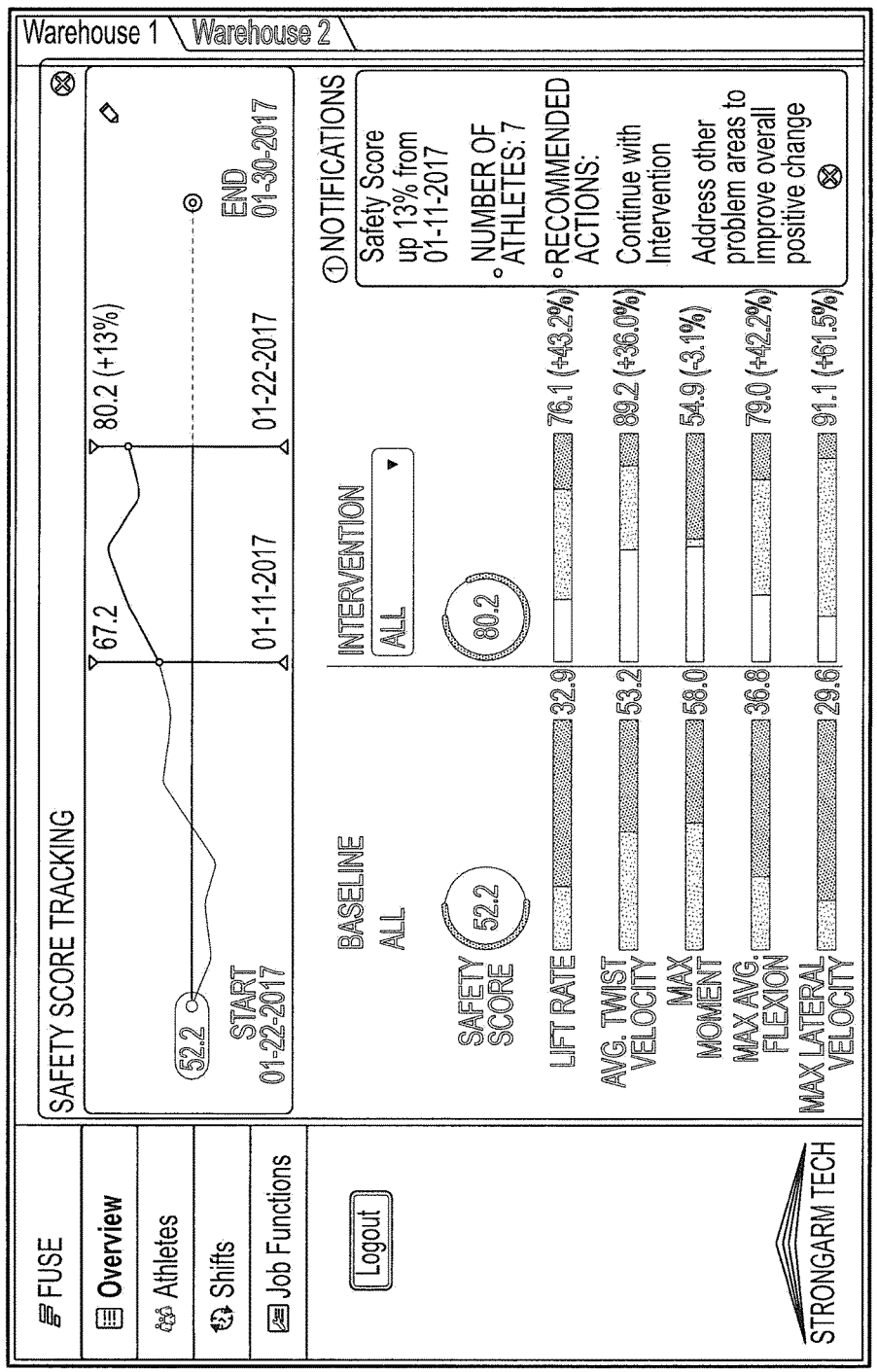
FIG. 12J is an exemplary display that is the exemplary display of FIG. 12I as configured to display data during a selected time interval.
Figure 12K:
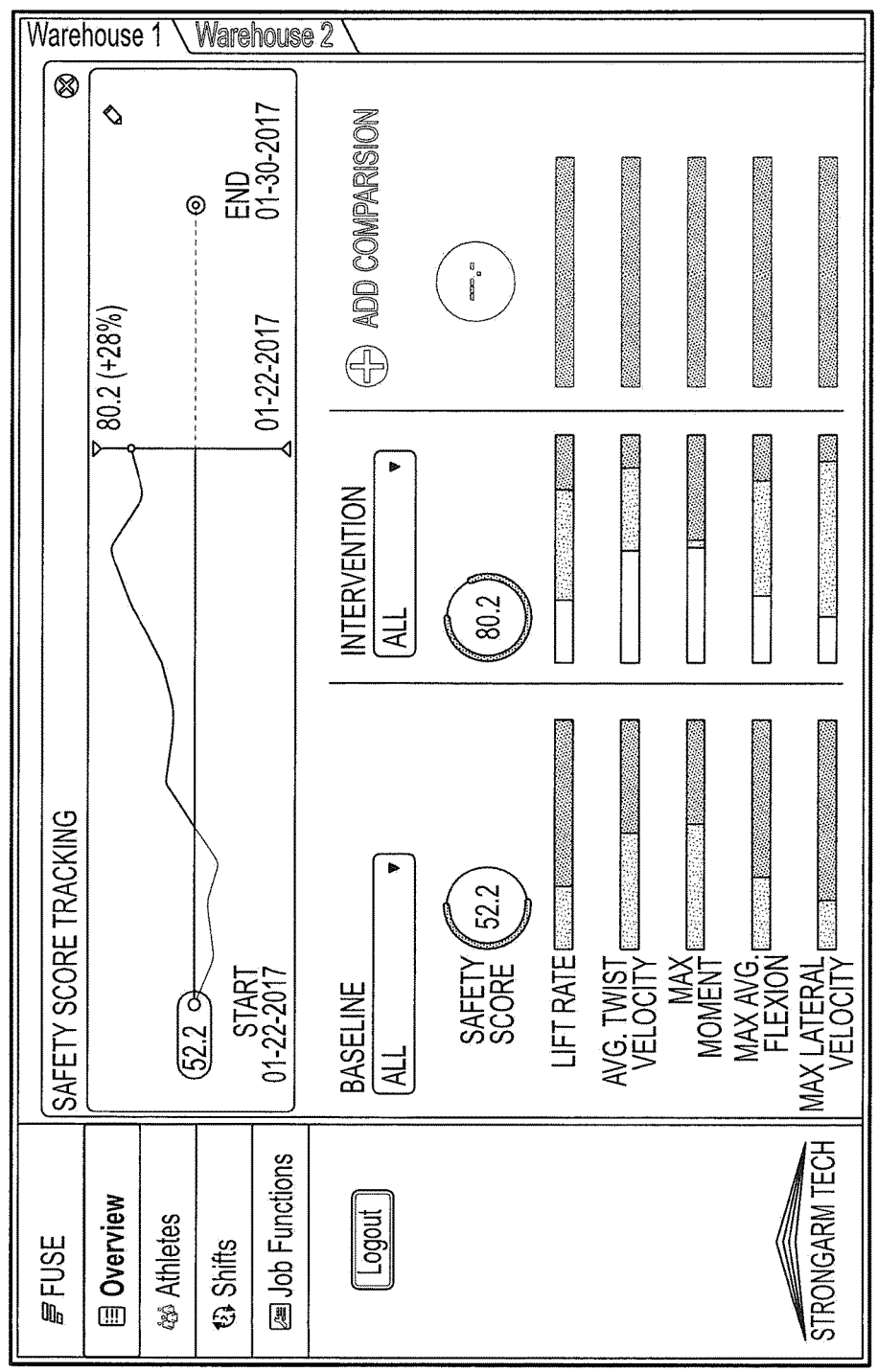
FIG. 12K is an exemplary display that is the exemplary display of FIG. 12I as configured to allow a selection of comparisons.
Figure 12L:
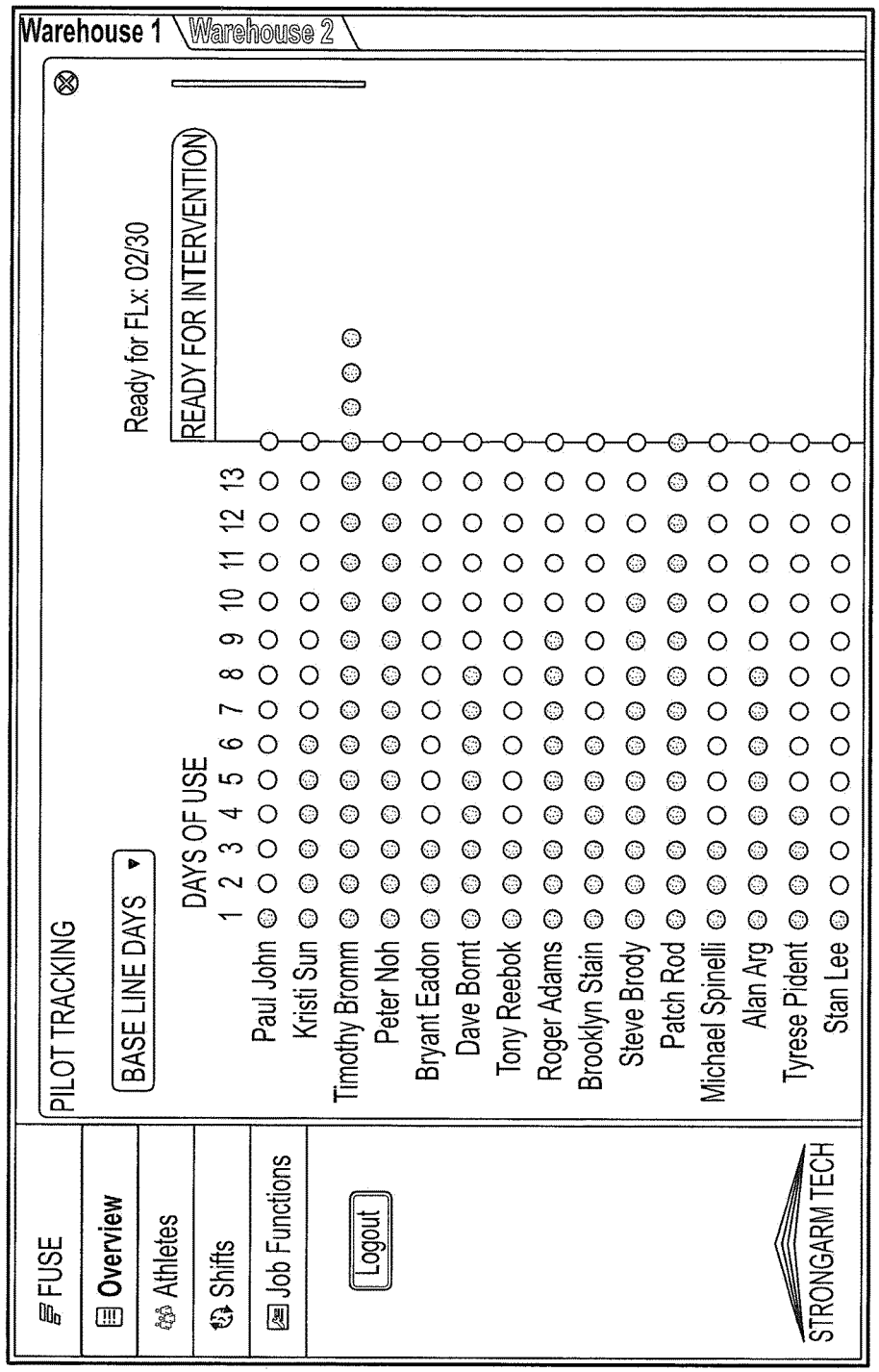
FIG. 12L is an exemplary display tracking recorded data for a group of individuals and indicating which individuals may be ready to receive an intervention.

FIG. 12I shows an exemplary display providing historical tracking of safety scores before and after an intervention. In the display of FIG. 12I, baseline safety scores and safety scores resulting from the intervention are shown. FIG. 12J shows an exemplary display that is the exemplary display of FIG. 12I as configured to display data during a selected time interval. In the display of FIG. 12J, it is indicated that a safety score has risen 13% over the selected time interval and a recommendation to continue interventions is provided. In some embodiments, interventions that have been successful (e.g., interventions that have achieved an increase in safety score greater than a certain threshold) are automatically continued. FIG. 12K shows an exemplary display that is the exemplary display of FIG. 12I as operated to allow a selection of comparisons (e.g., across specified time intervals). FIG. 12L shows an exemplary display tracking the recording for a group of individuals and indicating which individuals may be ready to receive an intervention. In the display of FIG. 12L, individuals for whom data has been recorded for fourteen days are indicated as ready to receive an intervention.

Figure 13A:
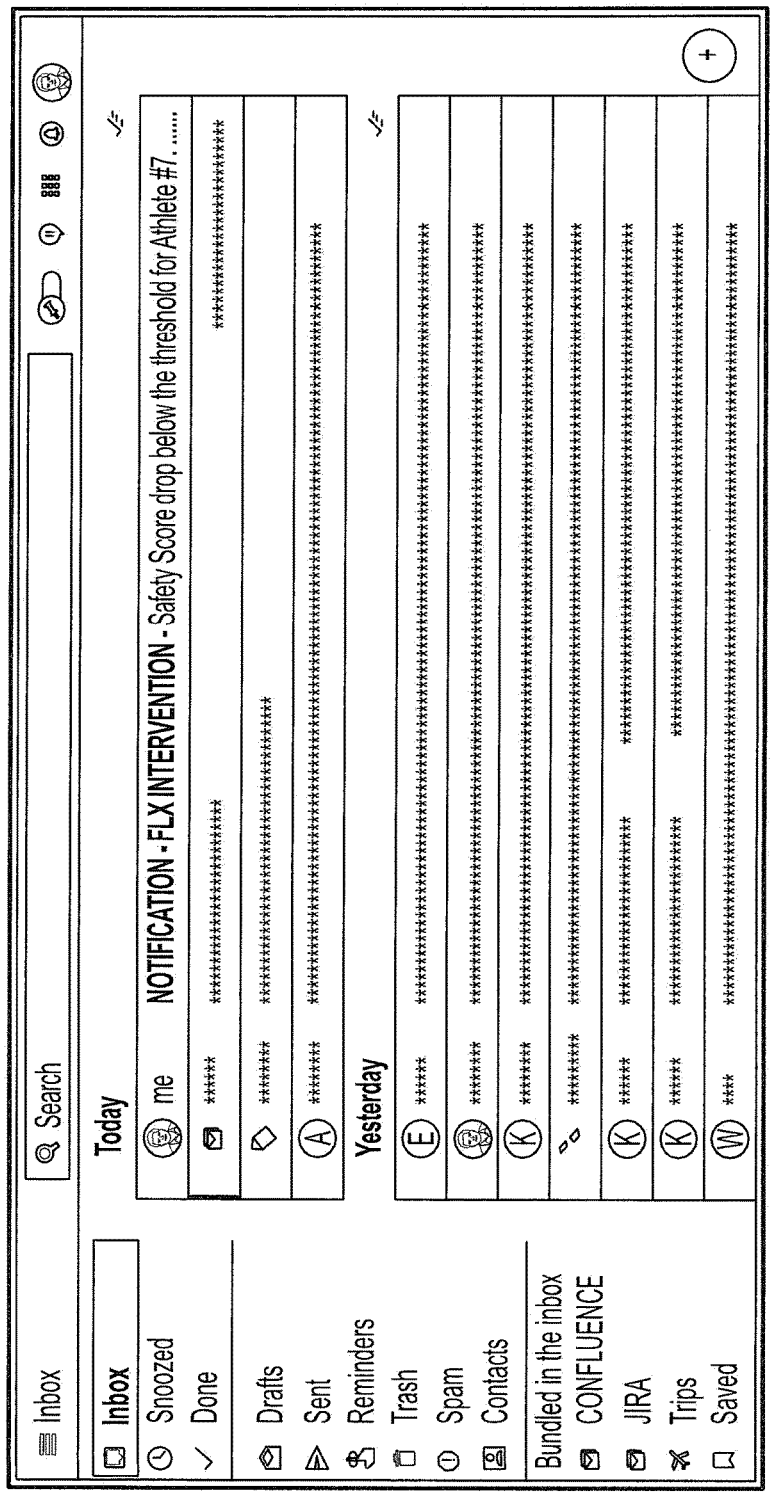
FIG. 13A is an exemplary display showing an intervention that is provided as an email to an individual.
Figure 13B:
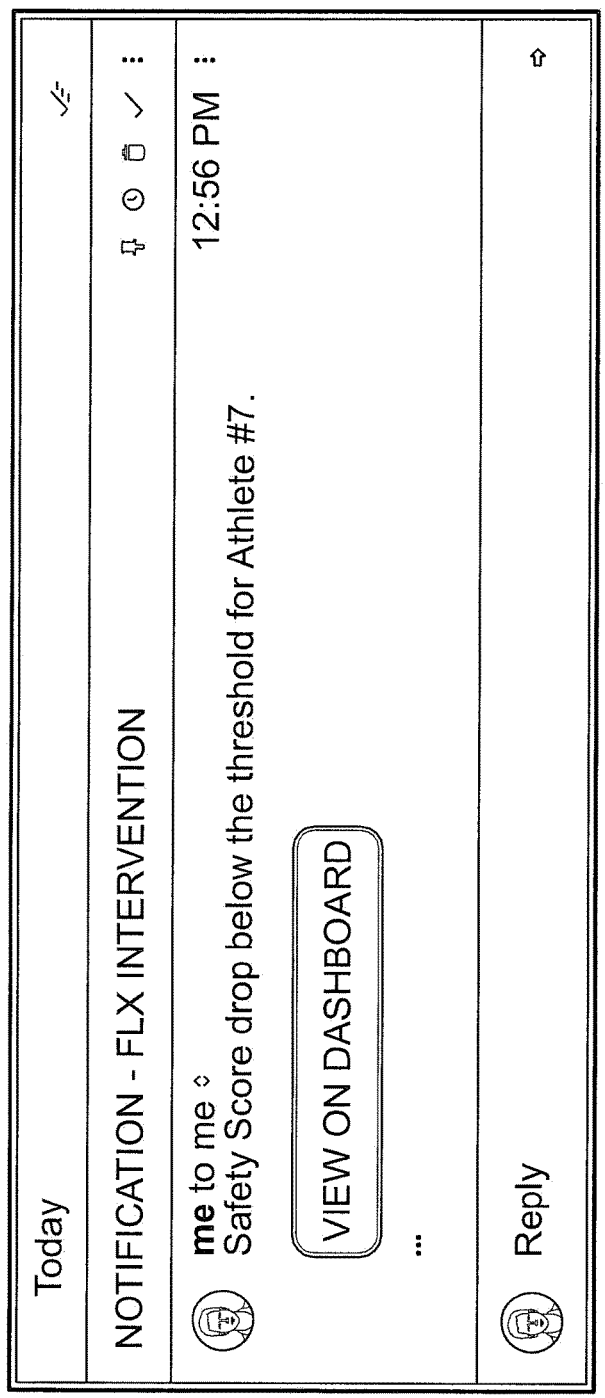
FIG. 13B is an exemplary display that is the display of FIG. 13A as operated to show further detail regarding the intervention.

FIG. 13A shows an exemplary display demonstrating a manner in which an intervention may take the form of an email sent to an individual (e.g., a wearer of the wearable sensor 112, a manager, etc.). The display of FIG. 13A shows an email inbox including an email containing intervention notification. FIG. 13B shows an exemplary display that may be displayed after the email containing the intervention notification is selected from the inbox shown in FIG. 13A. The display of FIG. 13B shows the reasons for triggering an intervention and provides a selectable button by means of which additional information may be displayed.

The above-described systems and methods can be implemented in digital electronic circuitry, in computer hardware, firmware, software, and any combination thereof. The implementation can be as a computer program product. The implementation can, for example, be in a machine-readable storage device, for execution by, or to control the operation of, data processing apparatus. The implementation can, for example, be a programmable processor, a computer, multiple computers, and any combination thereof.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can include, but is not limited to, FPGAs (field programmable gate arrays), ASICs (application-specific integrated circuits), and combinations thereof. Subroutines and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., network 110).

The system can include clients and servers. A client and a server are generally remote from each other and typically interact through a communication network. The relationship of client and server arises by virtue of computer programs running on the respective computers and having a client-server relationship to each other. The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a Markush group or other grouping is used herein, all individual members of the group and all combinations and sub-combinations possible of the group are intended to be individually included in the disclosure.

Every combination of components described or exemplified herein can be used to practice the disclosed embodiments, unless otherwise stated.

Whenever a range is given in the specification, for example, a temperature range, all intermediate ranges and sub-ranges, as well as all individual values included in the ranges given, are intended to be included in the disclosure. As used herein, ranges specifically include the values provided as endpoint values of the range. For example, a range of 1 to 100 specifically includes the end point values of 1 and 100.

It must be noted that as used herein, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

As used herein, "comprising" is synonymous with "including," "having", "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this disclosure.

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

What is claimed is:

1. A system, comprising:
   a wearable sensor unit configured to be worn by a person at one location on the person's body, the wearable sensor unit including a plurality of sensors configured to record sensor data during an activity performed by the person, the sensor data comprising accelerometer data, gyroscope data, and magnetometer data;
   an analysis element configured to:
      receive the sensor data from the wearable sensor unit, the sensor data including sensor orientation data of the wearable sensor unit during the activity, the sensor orientation data including (a) yaw data of the wearable sensor unit, (b) pitch data of the wearable sensor unit, and (c) roll data of the wearable sensor unit,
         wherein the yaw data of the wearable sensor unit represents an orientation of the wearable sensor unit with respect to a yaw axis and with respect to a neutral orientation,
         wherein the pitch data of the wearable sensor unit represents an orientation of the wearable sensor unit with respect to a pitch axis and with respect to a neutral orientation, the pitch axis being perpendicular to the yaw axis, and
         wherein the roll data of the wearable sensor unit represents an angle of orientation of the wearable sensor unit with respect to a roll axis and with respect to a neutral orientation, the roll axis being perpendicular to the pitch axis and to the yaw axis,
      determine a neutral posture of the person based on the sensor data recorded while the person is moving, wherein the neutral posture of the person includes a neutral posture yaw value, a neutral posture pitch value, and a neutral posture roll value,
      translate, by a processor programmed with at least one matrix translation algorithm, the sensor orientation data of the wearable sensor unit to person orientation data of the person during the activity, the person orientation data including (a) yaw data of the person, (b) pitch data of the person, and (c) roll data of the person,
         wherein the yaw data of the person represents an orientation of the person with respect to the yaw axis and with respect to the neutral posture of the person,
         wherein the pitch data of the person represents an orientation of the person with respect to the pitch axis and with respect to the neutral posture of the person, and
         wherein the roll data of the person represents an orientation of the person with respect to the roll axis and with respect to the neutral posture of the person,
      determine, for the person during the activity, (a) a lift rate, (b) a maximum sagittal flexion, (c) an average twist velocity, (d) a maximum moment, and (e) a maximum lateral velocity based on at least (a) the yaw data of the person, (b) the pitch data of the person, and (c) the roll data of the person, and
      determine a score representative of an injury risk to the person during the activity based on (a) the lift rate, (b) the maximum sagittal flexion, (c) the average twist velocity, (d) the maximum moment, and (e) the maximum lateral velocity; and
   a tangible feedback element configured to provide at least one tangible feedback based on the score so as to reduce the injury risk, the at least one tangible feedback comprising at least one of (a) at least one haptic feedback, (b) at least one audible feedback, (c) at least one visible feedback, (d) at least one physical item to assist the person to perform the activity, and (e) at least one instruction to assist the person to perform the activity.

2. The system of claim 1, wherein the score is either a risk score that is configured to increase as the injury risk increases or a safety score that is configured to decrease as the injury risk increases.

3. The system of claim 1, wherein the tangible feedback element is integrated with the wearable sensor unit.

4. The system of claim 3, wherein the tangible feedback element includes at least one of (a) at least one vibration motor configured to provide the at least one haptic feedback, (b) at least one speaker configured to provide the at least one audible feedback, (c) at least one display configured to provide the at least one visible feedback, and (d) at least one indicator light configured to provide the at least one visible feedback.

5. The system of claim 1, wherein the tangible feedback element is configured to provide tangible feedback when the injury risk to the person exceeds a predetermined threshold.

6. The system of claim 1, wherein the determining, for the person during the activity, (a) the lift rate, (b) the maximum sagittal flexion, (c) the average twist velocity, (d) the maximum moment, and (e) the maximum lateral velocity is further based on body geometry.

7. The system of claim 6, wherein the body geometry is body geometry of the person.

8. The system of claim 6, wherein the body geometry is predetermined.

9. The system of claim 1, wherein the wearable sensor unit includes an inertial measurement unit.

10. The system of claim 1, wherein the wearable sensor unit includes a mobile phone.

11. The system of claim 1, wherein the tangible feedback includes at least one physical item to assist the person to perform the activity, and wherein the physical item includes at least one of an ergoskeleton, eye protection, ear protection, respiratory protection, foot protection, and hazardous materials protection, temperature protection, and fall protection.

12. The system of claim 1, wherein the tangible feedback includes at least one instruction to assist the person to perform the activity, and wherein the at least one instruction to assist the person to perform the activity includes training to perform the activity.

13. The system of claim 1, wherein the tangible feedback includes at least one instruction to assist the person to perform the activity, and wherein the at least one instruction to assist the person to perform the activity includes a scheduling change.

14. The system of claim 13, wherein the scheduling change includes one of reassigning the person and switching the person with a further person.

15. The system of claim 1, further comprising:
a plurality of further wearable sensor units, each of which is configured to be worn by one of a plurality of further persons, each of the plurality of further wearable sensor units including a plurality of sensors configured to record sensor data during an activity performed by the one of the further persons, the sensor data comprising accelerometer data, gyroscope data, and magnetometer data,
wherein the analysis element is further configured to:
receive the sensor data from each of the plurality of further wearable sensor units,
determine sensor orientation data of each of the plurality of further wearable sensor units during the activity based on the sensor data received from each of the plurality of further wearable sensor units,
translate, by the processor programmed with the at least one matrix translation algorithm, the sensor orientation data of each of the plurality of further wearable sensor units to person orientation data of each of the plurality of further persons during the activity,
determine, for each of the further plurality of persons during the activity, (a) a lift rate, (b) a maximum sagittal flexion, (c) an average twist velocity, (d) a maximum moment, and (e) a maximum lateral velocity, and
determine a further plurality of scores, each of which is representative of an injury risk to one of the further plurality of persons.

16. The system of claim 15, wherein the tangible feedback element is configured to provide tangible feedback to at least some of the further plurality of persons based on the scores of the at least some of the further plurality of persons.

17. The system of claim 15, wherein the analysis element is further configured to determine an aggregate score for at least some of the further plurality of persons.

18. The system of claim 17, wherein the at least some of the further plurality of persons are selected based on one of a job role, a full-time status, a duration of employment, a shift assignment, an injury history, a work location, a worker characteristic, a time of day, and a manual selection.

19. The system of claim 17, wherein the tangible feedback element is configured to provide tangible feedback to the at least some of the further plurality of persons based on the aggregate score.

20. The system of claim 1, wherein the activity includes performing at least one lifting action.

21. The system of claim 1, wherein the analysis element is configured to translate the sensor orientation data of the wearable sensor unit to the person orientation data of the person during the activity using at least one Tait-Bryan rotation.

22. The system of claim 1, wherein the neutral posture yaw value, the neutral posture pitch value, and the neutral posture roll value correspond to a yaw value, a pitch value, and a roll value, respectively, of a most common posture.

23. The system of claim 1, wherein the neutral posture yaw value corresponds to a yaw value that is most common, wherein the neutral posture pitch value corresponds to a pitch value that is most common, and wherein the neutral posture roll value corresponds to a roll value that is most common.

* * * * *